(12) United States Patent
Tournaire et al.

(10) Patent No.: US 6,559,126 B2
(45) Date of Patent: May 6, 2003

(54) PEPTIDES BLOCKING VASCULAR ENDOTHELIAL GROWTH FACTOR (VEGF)-MEDIATED ANGIOGENESIS, POLYNUCLEOTIDES ENCODING SAID PEPTIDES AND METHODS OF USE THEREOF

(75) Inventors: Roselyne Tournaire, La Gaude (FR); Caroline Demangel, Coogee (AU); Claude Derbin, Gif sur Yvette (FR); Gerard Perret, Montmorency (FR); Jean-Claude Mazie, Asnieres sur Seine (FR); Jean Plouet, Toulouse (FR); Roger Vassy, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/822,270

(22) Filed: Apr. 2, 2001

(65) Prior Publication Data

US 2002/0068697 A1 Jun. 6, 2002

Related U.S. Application Data

(60) Provisional application No. 60/193,396, filed on Mar. 31, 2000.

(51) Int. Cl.$^7$ .............................. A61K 38/00; C07K 7/06
(52) U.S. Cl. .............................. 514/16; 514/2; 530/329; 530/350; 435/7.1; 435/4; 435/DIG. 35; 536/23.1; 536/23.51
(58) Field of Search .................... 514/16, 2; 530/329, 530/350; 435/7.1, 4, DIG. 35; 536/23.1, 23.51

(56) References Cited

U.S. PATENT DOCUMENTS 5,766,860 A    6/1998   Terman et al. ............. 435/7.2
5,955,311 A    9/1999   Rockwell et al.

FOREIGN PATENT DOCUMENTS

WO          00/64946        11/2000

OTHER PUBLICATIONS

Chen et al, J. Am. Chem. Soc. 1993, 115, 12591–92.*
Fairbrother, Wayne J., et al: "Novel Peptides Selected to Bind Vascular Endothelial Growth Factor Target the Receptor–Binding Site." Biochemistry vol. 37, No. 51, pp. 17754–17764, Dec. 22, 1998.

Wiesmann, Christian, et al.: "Crystal Structure of the Complex Between VEGF and a Receptor–Blocking Peptide." Biochemistry, vol. 37, No. 51, pp. 17765–17772, Dec. 22, 1998.

Muller, Y.A., et al.: "Vascular Endothelial Growth Factor: Crystal Structure and Functional Mapping of the Kinase Domain Receptor Binding Site"; Proceedings of the National Academy of Sciences of usa, National Academy of Science. Washington, US, vol. 94, No. 14, pp. 7192–7197, Jul. 1997.

Cortese, R., et al.: "Identification of Biologically Active Peptides Using Libraries Displayed on Phage." Current Opinion in Biotechnology, London, GB, vol. 6, No. 1, pp. 73–80, 1995.

Plouet, Jean, et al.: "Extracellular Cleavage of the Vascular Endothelial Growth Factor 189–Amino Acid Form by Urokinase is Required for its Mitogenic Effect." Journal of Biological Chemistry, vol. 272, No. 20, pp. 13390–13396, 1997.

Cheng, Shi–Yuan, et al.: "Suppression of Glioblastoma Angiogenicity and Tumorigenicity By Inhibition of Endogenous Expression of Vascular Endothelial Growth Factor." Proceedings of The National Academy of Sciences of the United States, vol. 93, No. 16, pp. 8502–8507, 1996.

Terman, B.I., et al.: "Identification of the KDR Tyrosine Kinase as a Receptor for Vascular Endothelial Cell Growth Factor." Biochemical and Biophysical Research Communications, Academic Press Inc., Orlando, FL, US, vol. 187, No. 3, pp. 1579–1586, Sep. 30, 1992.

Binetruy–Tournaire, Roselyne, et al.: "Identification of a Peptide Blocking Vascular Endothelial Growth Factor (VEGF)–Mediated Angiogenesis." European Molecular Biology Organization Journal, vol. 19, No. 7, pp. 1525–1533, Apr. 3, 2000.

* cited by examiner

Primary Examiner—T. D. Wessendorf
(74) Attorney, Agent, or Firm—Oblon, Spivak, McClelland, Maier & Neustadt, P.C.

(57) ABSTRACT

The present invention provides peptides which can interact with VEGF and inhibit VEGF interaction with KDR or anti-VEGF antibody thereby inhibiting VEGF mediated angiogenesis or angiogeneis related diseases, polynucleotide encoding the peptides, vectors containing the polynucleotides, pharmaceutical compositions containing the peptides, and methods of inhibiting angiogenesis with the peptides.

13 Claims, 15 Drawing Sheets

PEPTIDES BLOCKING VASCULAR ENDOTHELIAL GROWTH FACTOR (VEGF)-MEDIATED ANGIOGENESIS, POLYNUCLEOTIDES ENCODING SAID PEPTIDES AND METHODS OF USE THEREOF

BACKGROUND OF THE INVENTION

1. Field of the Invention

Angiogenesis, the formation of blood vessels by sprouting from pre-existing ones, is essential for the growth of solid tumors beyond 2–3 mm in diameter and for tumor metastasis (Folkman, 1995; reviewed in Bouck et al., 1996;). The generation of new capillaries involves a multistep process, which includes the dissolution of the membrane of the originating vessel, the endothelial cell migration and proliferation, and formation of a new vascular tube (Cliff, 1963; Schoefl, 1963; Ausprunck and Folkman, 1977). Suppression of any one of these steps would inhibit the formation of new vessels and therefore affect tumor growth and generation of metastases. Indeed, it has been estimated that the elimination of a single endothelial cell could inhibit the growth of 100 tumor cells (Thorpe et al., 1995). Moreover, endothelial cells are genetically stable and therefore unlikely to mutate into drug-resistant variants (Young, 1989; Kerbel, 1991; Boehm et al., 1997). Since they line the inside of blood vessels, they are easily accessible to circulating drugs. This feature suggests that anti-angiogenic therapies targeting endothelial cells may provide a promising mechanism for cancer treatment.

2. Discussion of the Background

So far, several angiogenic factors have been identified (reviewed in Folkman, 1995; Hanahan et al., 1996), including the particularly potent Vascular Endothelial Growth Factor (VEGF), also known as VPF or vasculotropin (reviewed in Ferrara, 1993; Ferrara and Davis-Smyth, 1997). Unlike other angiogenic factors, VEGF acts as an endothelial cell-specific mitogen during angiogenesis (Terman et al., 1992 and Ferrara, 1993). Antibodies raised against VEGF have been shown to suppress tumor growth in vivo (Kim et al., 1993), indicating that VEGF antagonists could have therapeutic applications as inhibitors of tumor-induced angiogenesis.

VEGF was purified initially from the conditioned media of folliculostellate cells and from a variety of tumor cell lines (Ferrara et al, 1989; Plouët et al., 1989; Myoken et al., 1991). It is a member of the cystine-knot family of growth factors, which also includes PDGF (Platelet Derived Growth Factor). Recently, a number of VEGF structural homologs have been identified: VEGF-B, VEGF-C, VEGF-D and Placenta Growth Factor (PlGF) (Klagsbrun and D'Amore, 1996; reviewed in Ferrara, 1999). The human gene encoding VEGF is organized into eight exons, separated by seven introns. Alternative splicing of mRNAs for the VEGF gene results in the generation of five different molecular species, having 121, 145, 165, 189, or 206 amino acid residues in the mature monomer (Tisher et al., 1991; Houck et al., 1991). Only VEGF$_{165}$, which lacks the residues encoded by exon 6, is the mature and active form of VEGF. It binds to heparin and cell surface heparan sulfate proteoglycans, and can be expressed as a free or as a cell membrane bound form (Houck et al., 1992). Two tyrosine kinase receptors have been identified for which VEGF acts as a high affinity ligand: a fins-like tyrosine kinase-1 (Flt-1 or VEGFR-1) and a kinase domain receptor (KDR/Flk-1 or VEGFR-2) (Matthews et al., 1991; Terman et al., 1991; De Vries et al., 1992; Millauer et al., 1993). Although Flt-1 binds VEGF with 50-fold higher affinity than KDR (De Vries et al., 1992), most of the VEGF angiogenic properties (mitogenicity, chemotaxis, and induction on morphological changes) are mediated by interaction with KDR (Waltenberger et al., 1994). Therefore, the interaction between VEGF and KDR is the most appropriate to interrupt in order to inhibit angiogenesis.

The screening of phage-displayed libraries is a powerful technique for identifying peptides mimicking protein surfaces (Smith, 1985; Hoess, 1993; Felici et al., 1995). Since each peptide is physically linked to a genetic particle, clones specifically binding a target molecule can be selected by consecutive cycles of in vitro biopanning and in vivo amplification. New agonists and antagonists for cell membrane receptors have been successfully identified using this process (Cwirla et al., 1990; Cortese et al., 1996), for example, RGD containing peptides that bind either the GPIIb/IIIa receptor on platelets (O'Neil et al., 1992) or the 5 1 integrin (Koivunen et al., 1993). The selected peptides were able to antagonize integrin-mediated cell adhesion.

The present inventors have identified peptides blocking the binding of VEGF to KDR. A random peptide library displayed on filamentous phages (Cortese et al., 1996) was screened using two parallel strategies. In the first, the peptide repertoire was screened with cells expressing recombinant KDR (Plouët et al., 1997) and in the second, with a monoclonal antibody raised against VEGF. Since this antibody blocked VEGF-dependent endothelial cell proliferation, we postulated that its antigen binding site mimics all or part of the VEGF interaction surface with KDR. Both strategies led to the isolation of peptides that compete with VEGF binding to KDR, including a peptide, ATWLPPR (SEQ ID NO:1), which specifically inhibited human endothelial cell proliferation in vitro. Moreover, it totally abolished VEGF-induced angiogenesis in vivo. ATWLPPR (SEQ ID NO:1), as a specific antagonist of VEGF-KDR interaction, may represent an effective anti-tumor agent.

SUMMARY OF THE INVENTION

Accordingly, it is one object of the present invention to provide a method for screening for peptides capable of interacting with VEGF.

It is another object of the present invention to provide novel peptides which inhibit the interaction of VEGF and KDR.

It is another object of the present invention to provide novel polynucleotide sequences which encode such peptides.

It is another object of this invention to provide vectors which comprise the polynucleotides encoding such peptides.

It is another object of this invention to provide methods of inhibiting angiogenesis and diseases affected by angiogenesis using such peptides.

It is another object of this invention to provide pharmaceutical compositions containing such peptides.

These and other objects, which will become apparent during the following detailed description, have been achieved by the inventors' discovery of the novel peptides disclosed herein.

DETAILED DESCRIPTION OF THE INVENTION

Figure 1A:
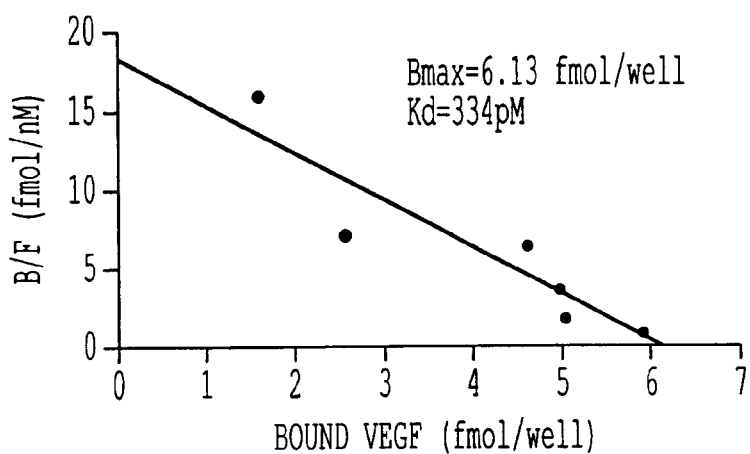
FIG. 1. CHO-KDR cells express a functional KDR. (A) Scatchard analysis of VEGF binding. The ratio of bound to free VEGF molecules (B/F) was plotted against bound VEGF concentration. (B) Effect of heparin. VEGF binding to CHO-KDR cells was measured in the presence of various amounts of heparin (C) Effect of PlGF. VEGF (100 ng/ml) binding to CHO-KDR cells was tested in absence (white bars) or presence (black bars) of heparin (1.8 m/ml), and compared to PlGF (50 ng/ml) or to PBS (control). Data correspond to the mean and standard deviations of triplicate samples. All binding experiments were performed twice and gave similar results.

All patent applications, patents and publications cited in this specification are hereby incorporated by reference in their entirety. In the case of inconsistencies, the present disclosure, including definitions, will prevail.

By peptides capable of interacting with VEGF, the invention covers any peptide or chemical product capable of inducing or modulating the activity of VEGF. For example, the activity of inhibiting VEGF properties involved in angiogenesis.

As used herein, "inhibit", "inhibiting" or "inhibition" includes any measurable reproducible reduction in the interaction of VEGF and KDR or anti-VEGF; angiogenesis; symptoms of diseases correlated to angiogenesis; or any other activities VEGF may mediate.

As used herein, an effective amount of a compound for treating a disorder is an amount that is sufficient to ameliorate, or in some manner reduce a symptom or stop or reverse progression of a condition. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

"consisting essentially of", in relation to amino acid sequence of a protein or peptide, is a term used hereinafter for the purposes of the specification and claims to refer to a conservative substitution or modification of one or more amino acids in that sequence such that the tertiary configuration of the protein or peptide is substantially unchanged. "Conservative substitutions" is defined by aforementioned function, and includes substitutions of amino acids having substantially the same charge, size, hydrophilicity, and/or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine. "Modification", in relation to amino acid sequence of a protein or peptide, is defined functionally as a deletion of one or more amino acids which does not impart a change in the conformation, and hence the biological activity, of the protein or peptide sequence.

Conventional amino acids are: alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine.

Additional amino acids that may be included in the peptide of the present invention include: Nle=L-norleucine; Aabu=.aminobutyric acid; Hphe=L-homophenylalanine; Nva=L-norvaline; Dala=D-alanine; Dcys=D-cysteine; Dasp=D-aspartic acid; Dglu=D-glutamic acid; Dphe=D-phenylalanine; Dhis=D-histidine; Dile=D-isoleucine; Dlys=D-lysine; Dleu=D-leucine; Dmet=D-methionine; Dasn=D-asparagine; Dpro=D-proline; Dgln=D-glutamine; Darg=D-arginine; Dser=D-serine; Dthr=D-threonine; Dval=D-valine; Dtrp=D-tryptophan; Dtyr=D-tyrosine; Dorn=D-omithine; Aib=arninoisobutyric acid; Etg=L-ethylglycine; Tbug=L-t-butylglycine; Pen=penicillamine; Anap=I-naphthylalanine; Chexa=cyclohexylalanine; Cpen=cyclopentylalanine; Cpro=aminocyclopropane carboxylate; Norb=aminonorbomylcarboxylate; Mala=L-α-methylalarnine; Mcys=L-α-methylcysteine; Masp=L-.alpha.-methylaspartic acid; Mglu=L-α-methylglutamic acid; Mphe=L-α-methylphenylalanine; Mhis=L α-methylhistidine; Mile=L-α-methylisoleucine; Mlys=L-α-methyllysine; Mleu=L-α-methylleucine; Mmet=L-α-methylmethionine; Masn=L-α-methylasparagine; Mpro= L-α-methylproline; Mgln=L-α-methylglutamine; Marg=L-α-methylarginine; Mser=L-a-methylserine; Mthr=L-α-methylthreonine; Mval=L-a-methylvaline; Mtrp=L-α-methyltryptophan; Mtyr=L-a-methyltyrosine; Morn=L-α-methylomithine;

Mnle=L-a-methylnorleucine; amino-α-methylbutyric acid;. Mnva=L-a-methylnorvaiine;

Mhphe=L-α-methylhomophenylalanine; Metg=L-a-methylethylglycine; methyl-γ-aminobutyric acid;, methylaminoisobutyric acid; Mtbug=L-α-methyl-t-butylglycine; methylpenicillamine; methyl-α-naphthylalanine; methylcyclohexylalanine; methylcyclopentylalanine; Dmala=D-α-methylalanine; Dmorn=D-α-methylomithine; Dmcys=D-α.-methylcysteine; Dmasp=D-α-methylaspartic acid; Dmglu=D-α-methylglutamic acid; Dmphe=D-α-methylphenylalanine; Dmhis=D-α-methylhistidine; Dmile=D-α-methylisoleucine; Dmlys=D-α-methyllysine; Dmleu=D-α-methylleucine; Dmmet=D-α-methylmethionine; Dmasn=D-α-methylasparagine; Dmpro=D-α-methylproline; Dmgln=D-α-methylglutamine; Dmarg=D-α-methylarginine; Dmser=D-α-methylserine; Dmthr=D-α-methylthreopine; Dmvai=D-α-methylvaline; Dmtrp=D-α-methyltryptophan; Dmtyr=D-α-methyltyrosine; Nmala=L-N-methylalanine; Nmcys=L-N-methylcysteine; Nmasp=L-N-methylaspartic acid; Nmglu=L-N-methylglutamic acid; Nmphe=L-N-methylphenylalanine; Nmhis=L-N-methylhistidine; Nmile=L-N-methylisoleucine; Nmlys=L-N-methyllysine; Nmleu=L-N-methylleucine; Nmmet=L-N-methylmethionine; Nmasn=L-N-methylasparagine; Nmchexa=N-methylcyclohexylalanine; Nmgln=L-N-methylglutamine; Nmarg=L-N-methylarginine; Nmser=L-N-methylserine; Nmthr=L-N-methylthreonine;

Nmval=L-N-methylvaline; Nmtrp=L-N-methyltryptophan; Nmtyr=L-N-methyltyrosine; Nmorn=L-N-methylomithine; Nmnle=L-N-methylnorleucine; Nmaabu=N-amino-α-methylbutyric acid; Nmnva=L-N-methylnorvaline; Nmhphe=L-N-methylhomophenylalanine; Nmetg=L-N-methylethylglycine; Nmgabu=N-methyl-γ-aminobutyric acid; Nmcpen=N-methylcyclopentylalanine; Nmtbug=L-N-methyl-t-butylglycine; Nmpen=N-methylpenicillamine; Nmanap=N-methyl-a-naphthylalanine; Nmaib=N-methylaminoisobutyric acid; Naeg=N-(2-aminoethyl)glycine; Dnmala=D-N-methylalanine; Dnmorn=D-N-methylomithine;

Dnmcys=D-N-methylcysteine; Dnmasp=D-N-methylaspartic acid; Dnmglu=D-N-methylglutamic acid; Dnmphe=D-N-methylphenylalanine; Dnmhis=D-N-methylhistidine; Dnmile=D-N-methylisoleucine; Dnmlys=D-N-methyllysine; Dnmleu=D-N-methylleucine; Dnmmet=D-N-methylmethionine; Dnmasn=D-N-methylasparagine; Dnmpro=D-N-methylproline; Dnmgln=D-N-methylglutamine; Dnmarg=D-N-methylarginine; Dnmser=D-N-methylserine; Dnmthr=D-N-methylthreonine; Dnmval=D-N-methylvaline; Dnmtrp=D-N-methyltryptophan; Dnmtyr=D-N-methyltyrosine; Nala=N-methylglycine (sarcosine); Nasp=N-(carboxymethyl)glycine; Nglu=N-(2-carboxyethyl)glycine; Nphe=N-benzylglycine; Nhhis=N-(imidazolylethyl)glycine; Nile=N-(1-methylpropyl)glycine; Nlys=N-(4-aminobutyl)glycine; Nleu=N-(2methyylpropyl)glycine; Nmet=N-(2- methylthioethyl)glycine; Nhser=N-(hydroxyethyl)glycine; Nasn=N-(carbamylmethyl)glycine; Ngln=N-(2-carbamylethyl)glycine; Nval=N-(1-methylethyl)glycine; Narg=N-(3-guanidinopropyl)glycine; Nhtrp=N-(3-indolylethyl)glycine; Nhtyr=N-(p-hydroxyphenethyl)glycine; Nthr=N-(1-hydroxyethyl)glycine; Ncys=N-(thiomethyl)glycine; Norn=N-(3-aminopropyl)glycine; Ncpro=N-cyclopropylglycine; Ncbut=N-cyclobutyglycine; Nchex=N-cyclohexylglycine; Nchep=N-cycloheptylglycine; Ncoct=N-cyclooctylglycine; Ncdec=N-cyclodecylglycine; Ncund=N-cycloundecylglycine;

Ncdod=N-cyclododecylglycine; Nbhm=N-(2,2-diphenylethyl)glycine;

Nbhe=N-(3,3-diphenylpropyl)glycine; Nnbhm=N-(N-(2,2-diphenylethyl)carbamylmethyl)glycine; Nnbhe=N-(N-(3,3-diphenylpropyl)carbamylmethyl)glycine; and Nbmc=1-carboxy-1-(2,2-diphenylethylamino)cyclopropane.

"consisting essentially of", in relation to a nucleic acid sequence, is a term used hereinafter for the purposes of the specification and claims to refer to substitution of nucleotides as related to third base degeneracy. As appreciated by those skilled in the art, because of third base degeneracy, almost every amino acid can be represented by more than one triplet codon in a coding nucleotide sequence. Further, minor base pair changes may result in variation (conservative substitution) in the amino acid sequence encoded, are not expected to substantially alter the biological activity of the gene product. Thus, a nucleic acid sequencing encoding a protein or peptide as disclosed herein, may be modified slightly in sequence (e.g., substitution of a nucleotide in a triplet codon), and yet still encode its respective gene product of the same amino acid sequence.

The term "expression vector" refers to an oligonucleotide which encodes the peptide of the invention and provides the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers. However, expression vectors may alternatively be viral recombinants designed to infect the host, or integrating vectors designed to integrate at a preferred site within the host's genome. Examples of viral recombinants are Adeno-associated virus (AAV), Adenovirus, Herpesvirus, Poxvirus, Retrovirus, and other RNA or DNA viral expression vectors known in the art. Examples of other expression vectors are disclosed in *Molecular Cloning: A Laboratory Manual*, Second Edition, Sambrook, Fritsch, and Maniatis, Cold Spring Harbor Laboratory Press, 1989.

Since its amino acid sequence has been disclosed by the present invention, the peptide of the present invention can be produced by a known chemical synthesis method (see, for example, a liquid phase synthesis method, a solid phase synthesis method, etc.; Izumiya, N., Kato, T., Aoyagi, H., Waki, M., "Basis and Experiments of Peptide Synthesis", 1985, Maruzen Co., Ltd.) based on that sequence.

The peptide of the present invention may contain one or more protected amino acid residues. The protected amino acid is an amino acid whose functional group or groups is/are protected with a protecting group or groups by a known method and various protected amino acids are commercially available.

When the peptide of the present invention is synthesized, it is preferred to select any of the protecting groups shown below. First, the protecting group for the α-amino group of an amino acid is Boc (t-butyloxycarbonyl) or Fmoc (9-fluorenylmethyloxycarbonyl). The protecting group for the guanidino group of arginine (Arg) is Tos (tosyl), NO.sub.2 (nitro), Mtr (4-methoxy-2,3,6-trimethylbenzenesulfonyl) or Pmc (2,2,5,7,8-pentamethylchroman-6-sulfonyl). The protecting group for the ε-amino group of lysine (Lys) is Z (benzyloxycarbonyl) or Cl.Z (2-cholorobenzyloxycarbonyl), Boc, or Npys (3-nitro-2-pyridinesulfenyl). The protecting group for the imidazolyl group of histidine (His) is Tos, Z, Pac (phenacyl), Bom (benzyloxymethyl), Dnp (dinitrophenyl), or Trt (trityl). The protecting group for the mercapto group of cysteine (Cys) is Bzl (benzyl), MBzl (4-methoxybenzyl), 4-MeBzl (4-methylbenzyl), Acm (acetamidomethyl), Trt, Npys, t-Bu (t-butyl), or t-BuS (t-butylthio). Preferred are MBzl, 4-MeBzl, Trt, Acm, and Npys. The protecting group for the hydroxyl group of tyrosine (Tyr) is Bzl, Cl.sub.2. Bzl (2,6-dichlorobenzyl), or t-Bu or the hydroxyl group of Tyr may be non-protected. The protecting group for the indole group of tryptophan (Trp) is CHO (formyl) or the indole group of Trp may be non-protected. The protecting group for the thiomethyl group of methionine (Met) is methyl sulfoxide or the thiomethyl group of Met may be non-protected. The protecting group for the hydroxyl group of serine (Ser) and threonine (Thr) is Bzl or t-Bu. The protecting group for the carboxyl group of aspartic acid (Asp) and glutamic acid (Glu) is OBzl (benzyl ester), OtBu (t-butyl ester), OcHex (cyclohexyl ester), OPac (phenacyl ester), etc. The protecting group for the carbamide group of asparagine (Asn) and glutamine (Gln) is Trt or Xan (xanthyl).

It is preferred that each protective group be selected appropriately from those known per se depending on the conditions of peptide synthesis.

The binding of the protected amino acid is achieved by usual condensation methods, for example, a DCC (dicyclohexylcarbodiimide) method, a DIPCDI (diisopropylcarbodiimide) method (Tartar, A., et al.; J. Org. Chem., 44, 5000 (1979)), an activated ester method, a mixed or symmetric acid anhydride method, a carbonyldiimidazole method, a DCC-HONSu (N-hydroxysuccinimide) method (Weygand, F., et al., Z. Naturforsch., B, 21, 426 (1966)), a DCC-HOBt (1-hydroxybenzotriazole) method (Koenig, W., et al.; Chem. Ber., 103, 788, 2024, 2034 (1970)), a diphenylphosphorylazide method, a BOP-HOBt method (Hudson, D., J. Org. Chem., 53, 617 (1988)) using a BOP reagent (benzotriazolyl-N-hydroxytrisdimethylaminophosphonium hexafluorophosphide), a HBTU (2-(1H-benzotriazol-1-yl)-1,1,3,3-tetramethyluronium hexafluorophosphate)-HOBt method (Knorr, R., et al., Tetrahedron Lett., 30, 1927 (1989)), a TBTU (2-(1H-benzotriazol-1-yl)-1,1,3,3-tetramethyluronium tetrafluoroborate)-HOBt method (Knorr, R., et al., Tetrahedron Lett., 30, 1927 (1989)), etc. However, among these methods, preferred are the DCC method, the DCC-HOBt method, the BOP-HOBt method, the HBTU-HOBt method, and the symmetric acid anhydride method.

The condensation reaction is usually carried out in an organic solvent such as dichloromethane, dimethylformamide (DMF), N-methylpyrrolidone (NMP) and the like or a mixed solvent composed of them.

As the eliminating reagent for the protective group of α-amino group, there can be used trifluoroacetic acid/dichloromethane, HCl/dioxane, piperidine/DMF or piperidine/NMP, etc. and these are selected appropriately depending on the kind of the protecting group.

The degree of progress of condensation reaction in each stage of synthesis can be examined by the method of E. Kaiser, et al. [Anal. Biochem., 34, 595 (1970)] (ninhydrin reaction).

As described above, a protected peptide resin having a desired amino acid sequence can be obtained.

Treatment of the protected peptide resin with hydrogen fluoride, TFMSA (trifluoromethanesulfonic acid) [E. Gross ed., Yajima, H., et al.; "The Peptide" 5, 65 (1983), Academic Press], TMSOTf (trimethylsilyl triflate [Fujii, N., et al.; J. Chem. Soc., Chem. Commun., 274 (1987)], TMSBr (trimethylsilylbromide [Fujii, N., et al.; Chem. Pharm. Bull., 35, 3880 (1987)], trifluoroacetic acid, or the like can eliminate the resin and protecting group simultaneously. The above-described eliminating reagent is selected appropriately depending on the strategy used (Boc or Fmoc) and the kinds of the resin and the protecting group. The peptide of the present invention can be produced by a series of the methods described above.

Alternatively, the peptide of the present invention can be produced by producing a polynucleotide (DNA or RNA) which corresponds to the amino acid sequence of the peptide of the present invention and producing a peptide by a genetic engineering technique using the polynucleotide. Polynucleotide coding sequences for amino acid residues are known in the art and are disclosed for example in *Molecular Cloning: A Laboratory Manual, Second Edition,* Sambrook, Fritsch, and Maniatis, Cold Spring Harbor Laboratory Press, 1989.

The peptide of the present invention thus produced can be purified by isolation/purification methods for proteins generally known in the field of protein chemistry. More particularly, there can be mentioned, for example, extraction, recrystallization, salting out with ammonium sulfate, sodium sulfate, etc., centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, etc. and combinations of these.

The peptide of the present invention which is produced can be hydrolyzed with an acid, for example, hydrochloric acid, methanesulfonic acid or the like and its amino acid composition can be examined by a known method. By this, it can be presumed whether or not the peptide of the present invention is produced correctly.

More strictly, the amino acid sequence of the produced peptide is determined by a known amino acid sequence determination method (for example, Edman degradation technique, etc.) to confirm whether the peptide of the present invention is produced correctly.

The peptide of the present invention includes a form of a salt thereof. As described later on, the peptide of the present invention is particularly useful as a medicine and hence the salt of the peptide is preferably a pharmaceutically acceptable salt.

The peptide of the present invention may form a salt by addition of an acid. Examples of the acid include inorganic acids (such as hydrochloric acid, hydrobromic acid, phosphoric acid, nitric acid, and sulfuric acid) or organic carboxylic acids (such as acetic acid, propionic acid, maleic acid, succinic acid, malic acid, citric acid, tartaric acid, and salicylic acid), acidic sugars such as glucuronic acid, galacturonic acid, gluconic acid, ascorbic acid, etc., acidic polysaccharides such as hyaluronic acid, chondroitin sulfates, alginic acid, or organic sulfonic acids (such as methanesulfonic acid, and p-toluenesulfonic acid), and the like. Of these salts, preferred is a pharmaceutically acceptable salt.

The peptide of the present invention may form a salt with a basic substance. Examples of the salt include, for example, pharmaceutically acceptable salts selected from salts with inorganic bases such as alkali metal salts (sodium salt, lithium salt, potassium salt, etc.), alkaline earth metal salts, ammonium salts, and the like or salts with organic bases, such as diethanolamine salts, cyclohexylamine salts, and the like.

The pharmaceutically acceptable carrier which can be used in the present invention is not limited particularly and includes an excipient, a binder, a lubricant, a colorant, a disintegrant, a buffer, an isotonic agent, a preservative, an anesthetic, and the like which can be used in a medical field.

The medicine of the present invention can be applied by any suitable administration method depending on the purpose of treatment and selected from injection (subcutaneous, intracutaneous, intravenous, intraperitoneal, etc.), eye dropping, instillation, percutaneous administration, oral administration, inhalation, and the like.

Also, the dosage form such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like can be selected appropriately depending on the administration method, and the peptide of the present invention can be accordingly formulated. Formulation in general is described in Chapter 25.2 of Comprehensive Medicinal Chemistry, Volume 5, Editor Hansch et al, Pergamon Press 1990.

The dose of the medicine of the present invention should be set up individually depending on the purpose of administration (prevention, maintenance (prevention of aggravation), alleviation (improvement of symptom) or cure); the kind of disease; the symptom, sexuality and age of patient; the administration method and the like and is not limited particularly.

Antibodies which react specifically with the inventive peptides are also included in the present invention. Methods of generating antibodies directed to a specific peptide fragment are known in the art. Examples of such methods are disclosed in Antibodies, A Laboratory Manual, Harlow and Lane, Cold Spring Harbor Press, 1988, herein incorporated by reference.

Having generally described this invention, a further understanding can be obtained by reference to certain specific examples which are provided herein for purposes of illustration only, and are not intended to be limiting unless otherwise specified.

EXAMPLES

Materials and Methods

Cell lines. KDR-expressing cells (CHO-KDR) were obtained by transfecting glycosaminoglycan-deficient pgsA 745 Chinese hamster ovary (CHO) cells (Esko, 1991) with the psV-7d expression vector (Plouët et al., 1997). CHO cells and CHO-KDR cell line were grown routinely in Dulbecco's modified Eagle's medium (DMEM) supplemented with 10% (v/v) fetal calf serum, 50 units/ml penicillin, 50 g/ml streptomycin, and 2 mM L-glutamine. Calf pulmonary artery endothelial cells (CPAE) were kindly provided by Dr. Binétruy (CNRS UPR 9079, Villejuif, France) and grown in minimum Eagle medium (MEM) supplemented with 20% (v/v) fetal calf serum, 50 units/ml penicillin, 50 g/ml streptomycin, and 2 mM L-glutamine. Human Umbilical Artery Endothelial Cells (HUAE) were grown routinely on gelatinized-dishes in EGM medium supplemented with antibiotics and 15% (v/v) fetal calf serum. Stock HUAE cultures were maintained by addition of 1 ng/ml VEGF every other day. The NIH3T3 fibroblast cell line was grown routinely in MEM medium supplemented with antibiotics and 10% (v/v) fetal calf serum.

Library screening with anti-VEGF antibody. Biopanning was adapted from the Ph.D.-7 kit standard procedure (New England Biolabs, Beverly, Mass.). Anti-human VEGF monoclonal antibody (V-4758, Sigma, St Louis, Mo.) was used to coat microtiter plates at 10 g/ml. Three rounds of selection were performed with non-specific elution of bound phages in pH 2.2 acidic buffer. To analyze the selected clones, overnight cultures of *E. coli* (strain ER2537) were diluted 1:100, infected with single clones, grown for 5 h with shaking at 37 C., and the culture supernatant containing phage particles was harvested. This phage stock was used to perform ELISA binding assays and to determine the peptide encoding sequence as described in the Ph.D.-7 kit guidelines.

Library screening with CHO-KDR cells. The selection procedure was adapted from Watters et al. (1997). Four rounds of biopanning were performed by incubating $10^{11}$ phage particles with $2\times10^6$ CHO-KDR cells. The last amplified eluate was then absorbed twice on $2\times10^6$ non-recombinant CHO cells to enrich for phage clones specifically binding KDR.

DNA and amino acid sequence analysis. Peptide sequences were analyzed with the GCG software package (Wisconsin, USA). A multiple sequence alignment performed by 'Pileup' analysis was used to determine the groups of related peptides. 'Gap' analysis was used to find an optimal alignment between the consensus motifs and the VEGF primary sequence.

ELISA of the phage-displayed peptide binding to CHO-KDR cells. Exponentially growing CHO-KDR cells were seeded in 96-well microtiter plates at $7\times10^4$ cells/well and left overnight at 37 C. Cells were fixed with paraformaldehyde (4% in PBS) for 15 min at room temperature and washed with PBS. Wells were then filled with PBS-Glycine 0.2%, kept for 15 min at room temperature and then washed with PBS. Phage particles ($10^{12}$ or $10^{13}$/Ml) were added to each well and incubated 2 h at room temperature. Wells were washed with PBS and the amount of bound phage was detected with peroxidase-conjugated anti-M13 phage serum (Pharmacia Biotech, Uppsala, Sweden).

Competition assay of binding to CHO-KDR cells. CHO-KDR cells were seeded in 24-well plates at a density of $5\times10^5$ cells/well. After 24 h, subconfluent plates were transferred at 4 C., and all subsequent operations were done at 4 C. Cells were washed twice with PBS, and incubated with $^{125}$I-VEGF (30 000 cpm, Amersham, Buckinghamshire, UK) in binding buffer (DMEM medium supplemented with 20 mM Hepes, pH 7.4, and 2 mg/ml gelatine). Various concentrations of unlabelled human recombinant VEGF (Pharmingen, San Diego, Calif.), heparin (Sigma, St Louis, Mo.), placenta growth factor (PlGF, R & D Systems, Minneapolis, Minn.) or peptides (Neosystem, Strasbourg, France) were added in a final volume of 0.3 ml. After 3 h, cells were washed five times with binding buffer and solubilized by the addition of 0.5 M NaOH. The amount of radioactivity bound to the cells was counted in a gamma counter (LKB 1261 Multigamma). The receptor affinity and the number of binding sites per cell were determined by Scatchard's analysis (Scatchard, 1986).

Cell proliferation assay. To test the anti-VEGF antibody neutralizing effect, CPAE cells were plated into 96-well tissue culture plates at a density of 500 cells/well. After 24 h, various concentrations of anti-VEGF antibody were added. The cells were cultured for an additional day and cell proliferation was measured using the Cell proliferation ELISA kit from Boerhinger (Indianapolis, Ind.). Cells were incubated with BrdU for 4 h at 37 C., and the incorporation of BrdU in newly synthetized DNA was quantified by immunoassay as described by the manufacturer. To investigate the peptide effect, after 24 h of CPAE cell growth, $2.1\times10^{-4}$M synthetic peptides were added daily to the culture medium. Cell proliferation was assessed after 24 h, 48 h or 72 h as described above. HUAE cells were seeded at 5,000 cells/well in 12 well plates in medium containing 2 ng/ml VEGF or 100 ng/ml immunopurified KDR anti-idiotypic antibodies (Ortega et al, 1997), and supplemented daily with various concentrations of V1 or V5 peptide. Cells were trypsinized and counted after 5 days using a Coulter counter.

Rabbit corneal pocket assay. Slow releasing implants of hydrogel (2×1 mm) were rehydrated with 2 1 PBS containing 25 g of bovine serum albumin and 2 pmol VEGF in the presence or absence of 30 nmol peptide. These implants were inserted in New Zealand rabbit (Elevage du Trottis, Esperce, France) corneal stroma 2 mm away from the limbus (Favard et al, 1991). Neovascularization was assessed on day 12 by direct examination with a slit lamp and scored according to a 4 grade scale (grade 1: less than 1 mm long neovessels, grade 2: 1 mm long neovessels, grade 3: 1 to 2 mm long neovessels, grade 4: neovessels extending to the implant). Means and standard deviations were determined on 8 implant groups for each condition.

Results

CHO-KDR Cells Express a VEGF Binding KDR

Figure 1B:
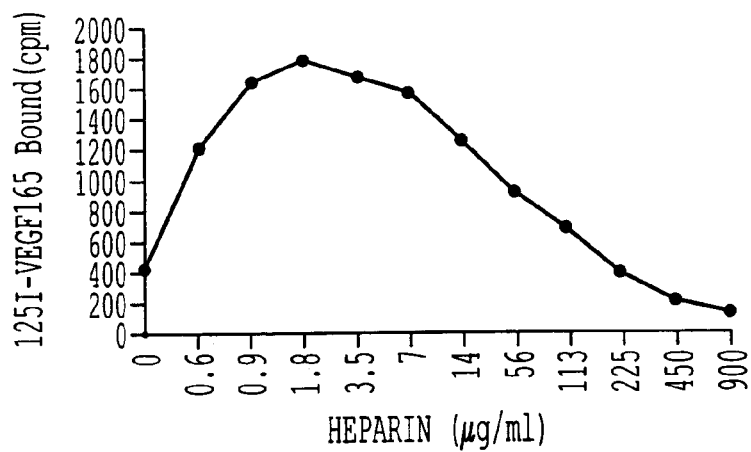
Figure 1C:
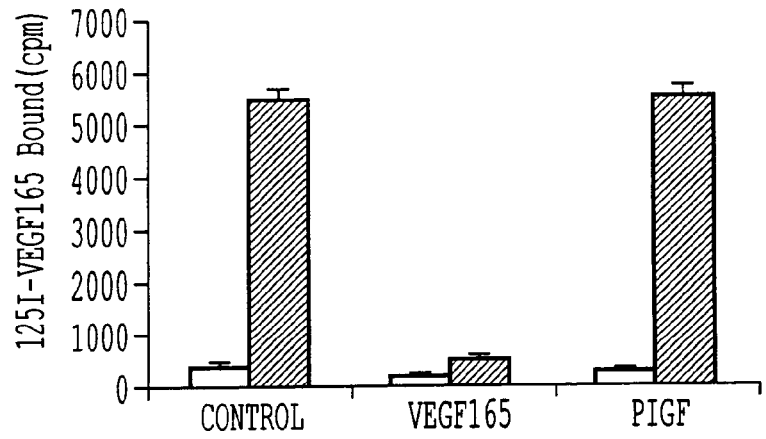

In order to find peptides binding KDR, we first looked for a receptor that we could use to perform panning techniques. CHO cells expressing a recombinant KDR at their membrane surface were tested for their ability to bind VEGF in a variety of conditions. FIG. 1A shows that the dissociation constant of VEGF on CHO-KDR cells was 334 pM. Heparin was able to increase the binding of VEGF to CHO-KDR cells, the optimal concentration being 1.8 µg/ml (FIG. 1B) and PlGF was not modifying VEGF binding to CHO-KDR cells (FIG. 1C). Taken together, all these data suggested that the KDR expressed by recombinant CHO cells exhibited the same characteristics as the endothelial receptor for binding to VEGF.

Identification of Peptides Binding Specifically to KDR

Since this receptor was able to bind VEGF, we tried to find peptides able to mimic this interaction and that bound KDR in the same conditions. A random 7-mer library composed of $2\times10^9$ independent clones was screened by binding to CHO-KDR cells. At the end of the selection, 24 clones were isolated and analyzed. DNA sequencing showed that seven independent peptides had been selected (K1 to K7), with no sequence homology (Table I).

Figure 2A:
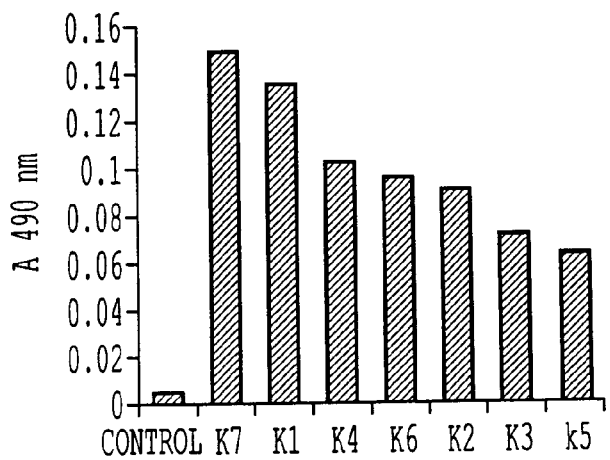
FIG. 2. Selected phage-displayed peptides bind to KDR specifically in ELISA. Clones selected by KDR binding ($10^{13}$ pfu/ml) (A) or by anti-VEGF antibody binding ($10^{12}$ pfu/ml) (B) were compared with M13 phage particles (control). Results are representative of three independent assays.

The binding of each selected clone to KDR was tested by ELISA on CHO-KDR cells. All the clones gave an ELISA signal significantly higher than the control bacteriophage one (FIG. 2A). However, ELISA signals were detectable only for phage concentrations higher than $10^{13}$/ml, suggesting that the selected peptides could bind KDR specifically, but with low affinity.

TABLE I

DNA sequence of the peptides selected by binding to CHO-KDR cells or to the anti-VEGF antibody

| Selection on CHO-KDR cells | | Selection on anti-VEGF antibody | |
|---|---|---|---|
| K1 | YLTMPTP (SEQ ID NO:8) | V1 | ATWLPPR (SEQ ID NO:1) |
| k2 | WPTPPYA (SEQ ID NO:9) | V2 | NPRALNY (SEQ ID NO:2) |
| K3 | TPHNTVS (SEQ ID NO:10) | V3 | ANLFKAK (SEQ ID NO:3) |
| K4 | SLPAHAR (SEQ ID NO:11) | V4 | YNSSFQA (SEQ ID NO:4) |
| K5 | HSSLQTP (SEQ ID NO:12) | V5 | ILDNYKL (SEQ ID NO:5) |
| K6 | YSIPKSS (SEQ ID NO:13) | V6 | LPPNPTK (SEQ ID NO:6) |
| K7 | ALQPRYL (SEQ ID NO:14) | V7 | YAIMPLV (SEQ ID NO:7) |

An Anti-VEGF Antibody Blocking VEGF-KDR Interaction

Figure 3:
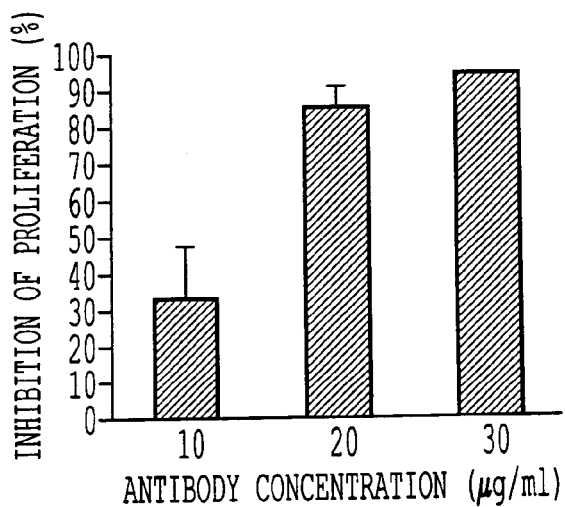
FIG. 3. The anti-VEGF antibody blocks CPAE cell growth. CPAE cell growth was measured in cultures supplemented with various concentrations of anti-VEGF antibody and compared with untreated cultures. Data represent means and standard deviations of proliferation inhibition for triplicate samples and are representative of two independent experiments.
Figure 4A:
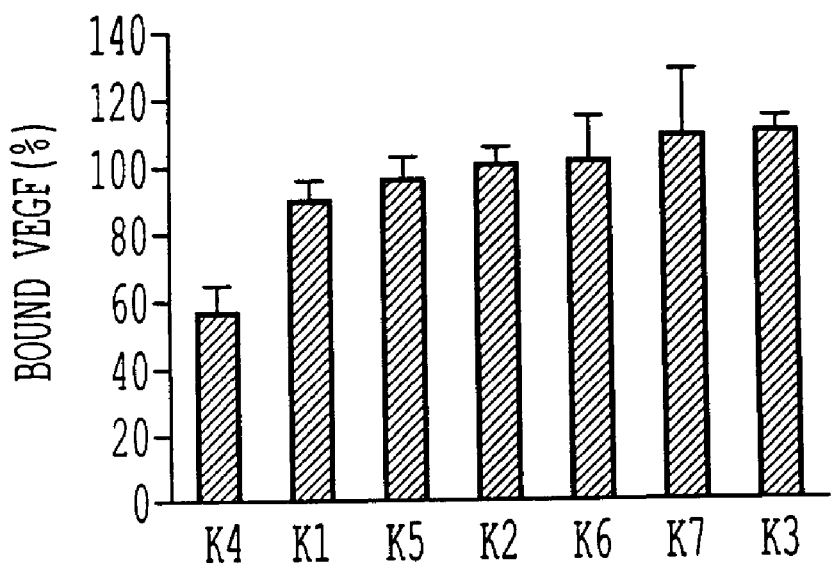
FIG. 4. Synthetic peptides compete with VEGF for KDR binding. Peptides selected by KDR binding (A) or by anti-VEGF binding (B) were tested in competition with VEGF for binding to CHO-KDR cells at the concentration of $2.1 \times 10^{-4}$ M and in the presence of heparin (1.8 g/ml). Data represent the means and standard deviations of triplicate samples. Similar results were obtained in three independent experiments.
Figure 4B:
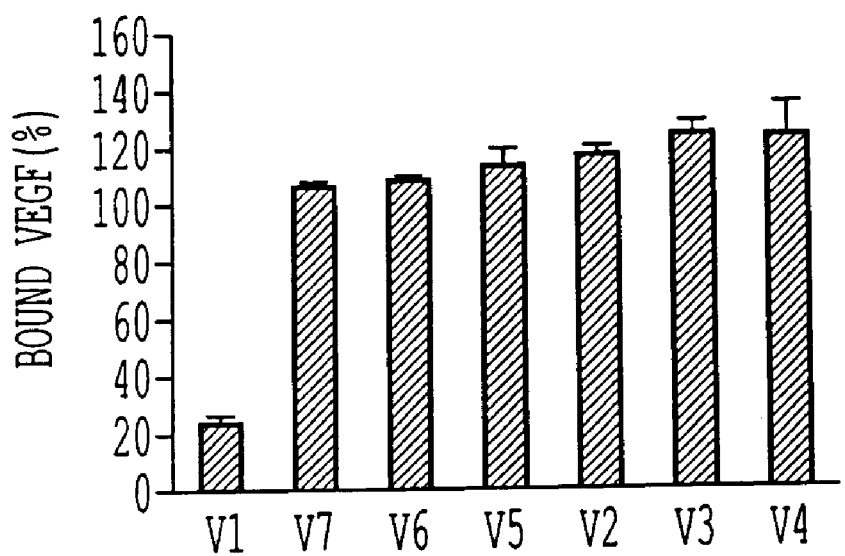
Figure 5A:
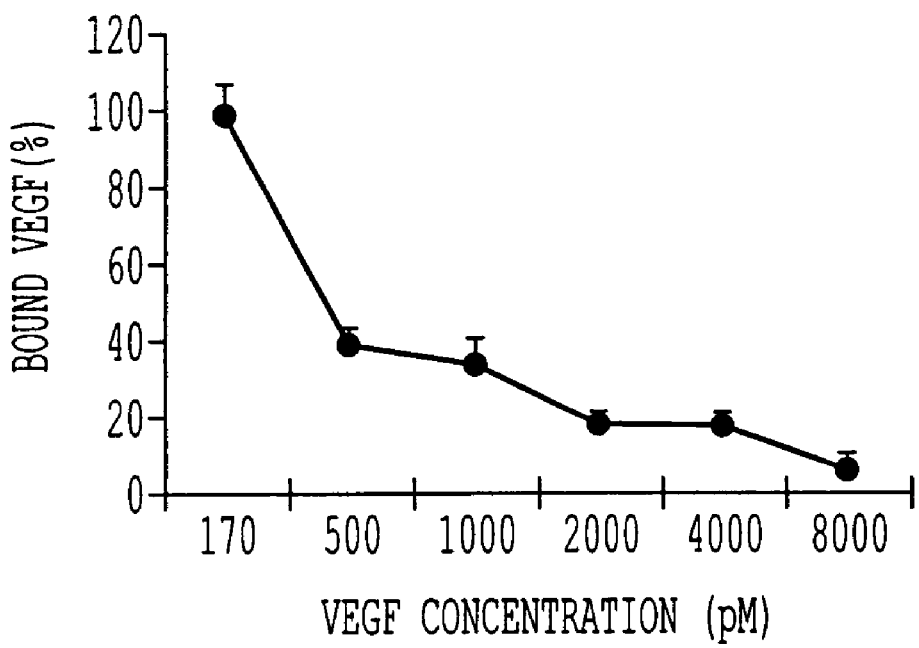
FIG. 5. V1 can abolish VEGF binding to KDR. Various concentrations of VEGF (A) or of V1 peptide (B) were tested in competition with radioactive-labelled VEGF for binding to CHO-KDR cells. As a uninhibitory control, V5 was tested in the same conditions. Data represent the mean and standard deviations of triplicate samples. Similar results were obtained in two different experiments.
Figure 5B:
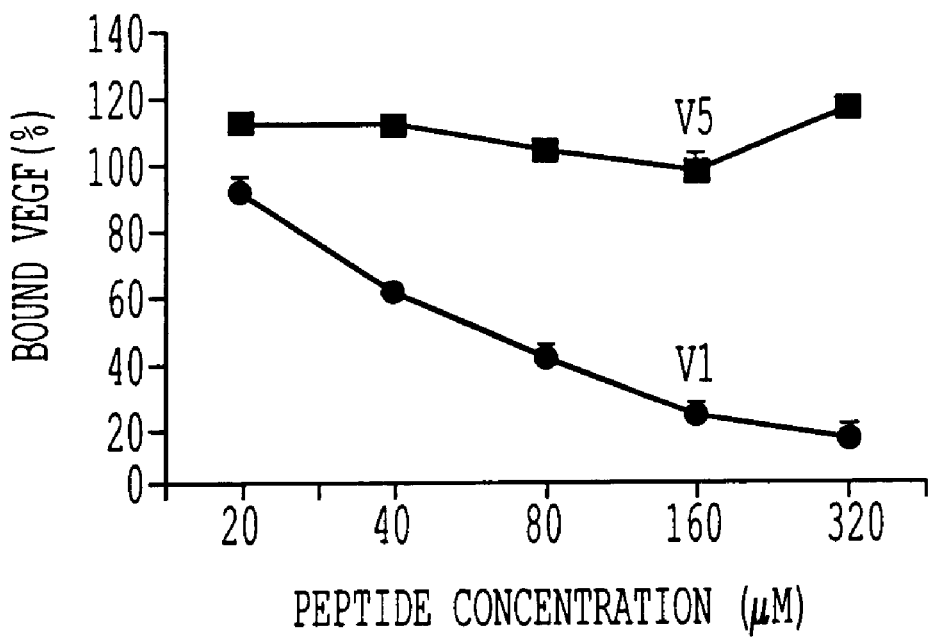
Figure 6A:
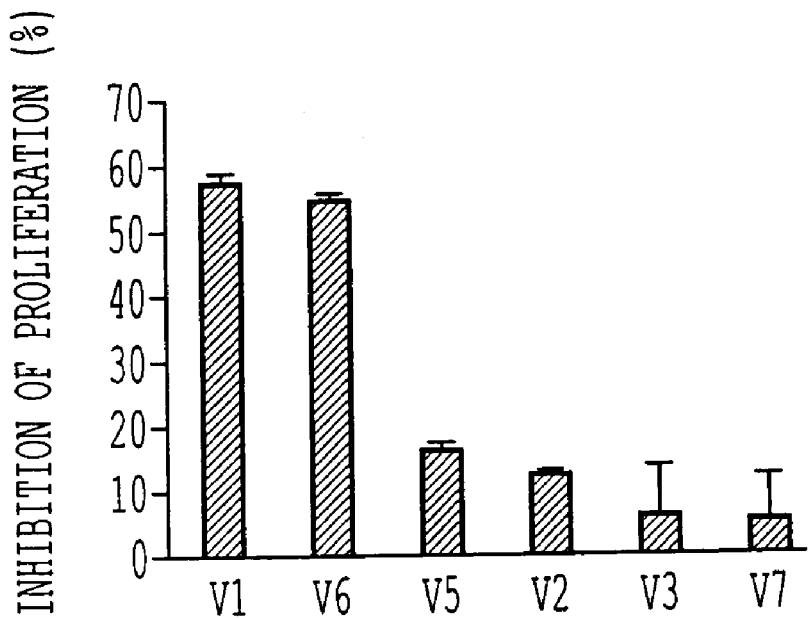
FIG. 6. V1 inhibits CPAE cell proliferation. CPAE cell growth was measured after 24 h of incubation in presence of synthetic peptides selected by antibody binding (A) or by KDR binding (B) and compared with untreated cultures. Data represent means and standard deviations of proliferation inhibition for triplicates and are representative of three independent experiments.
Figure 6B:
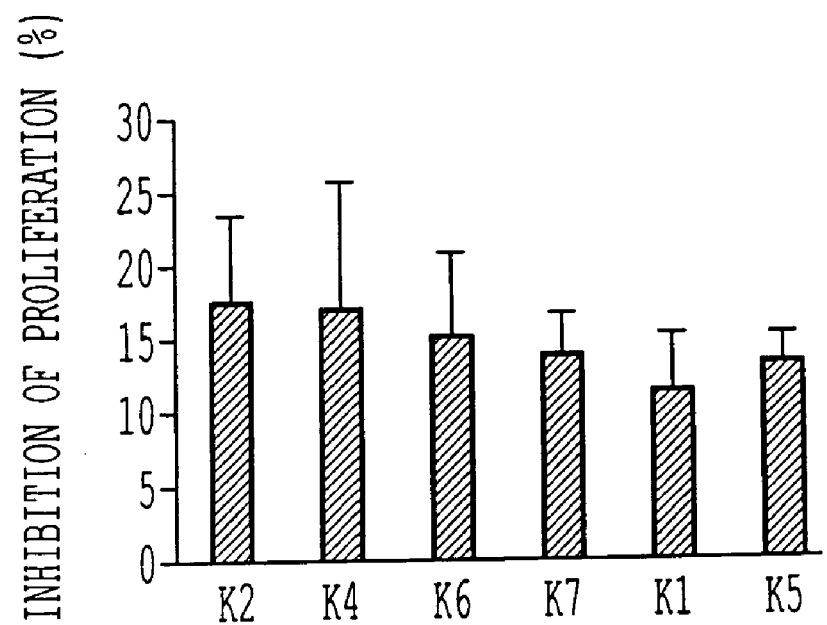
Figure 7A:
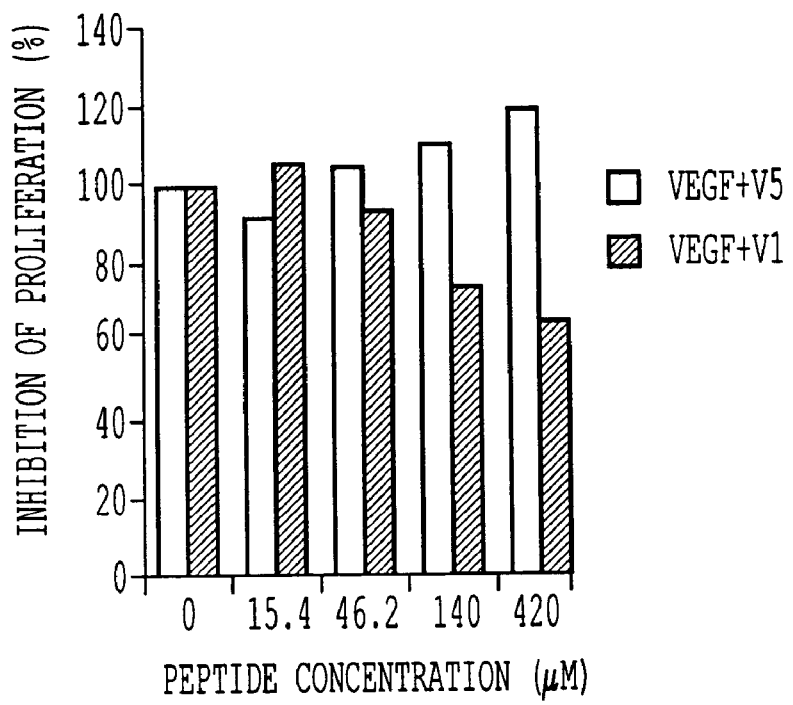
FIG. 7. V1 inhibits the proliferation of human endothelial cells induced by VEGF or by AIA in a dose dependent manner. HUAE cell cultures were grown in presence of VEGF (A) or anti-idiotypic antibodies (B), and were supplemented daily with various concentrations of V1 or V5. Cells were counted after 5 days. Data are means of proliferation inhibition percentages for triplicate samples.
Figure 7B:
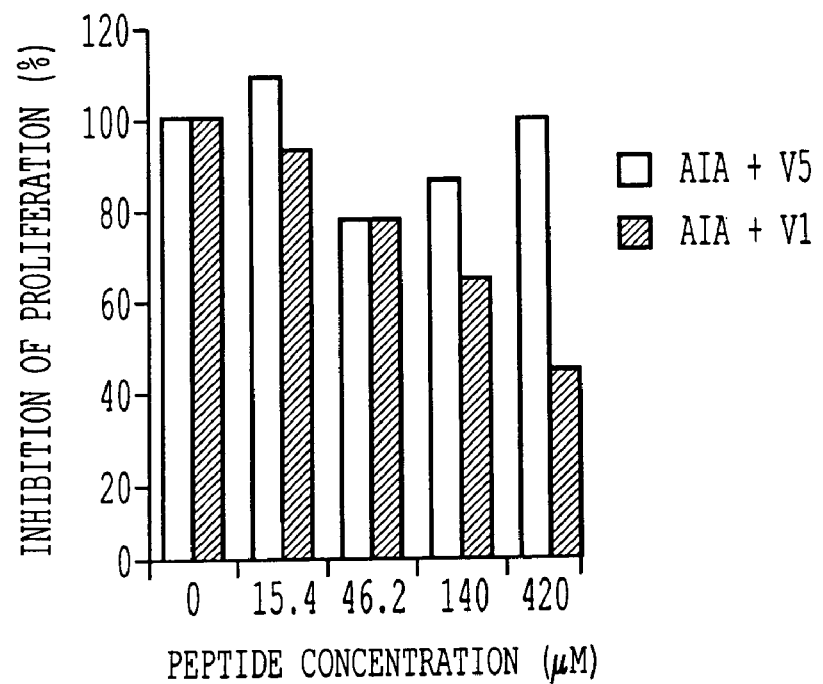
Figure 8:
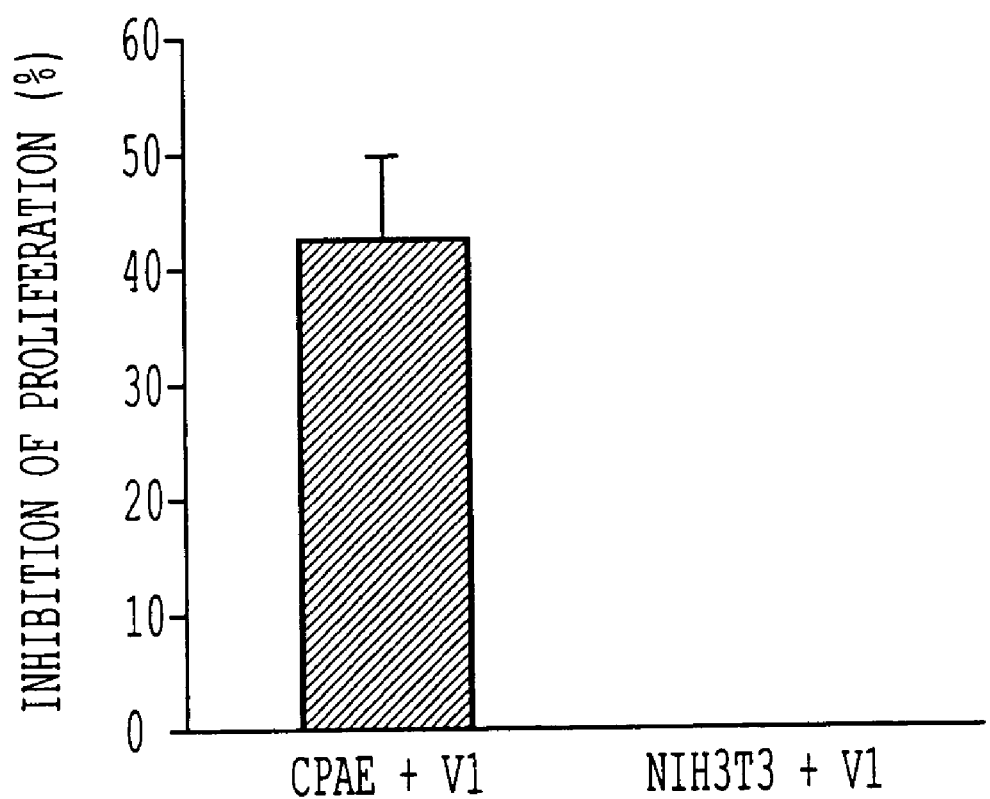
FIG. 8. V1 acts specifically on endothelial cells. CPAE and NIH 3T3 fibroblasts were cultured with or without V1 peptide, and the changes in cell proliferation were measured after 24 h. Data represent the means and standard deviations of proliferation inhibition percentages for triplicate samples, and similar results were obtained in two independent experiments.
Figure 9A:
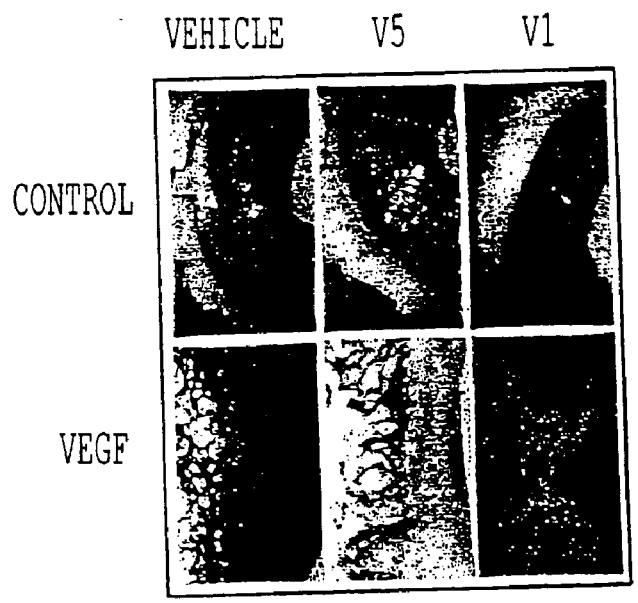
FIG. 9. V1 inhibits corneal angiogenesis in vivo. The neovascularization in implants containing V1, V5, or PBS (vehicle), in the presence or absence of VEGF was assessed 12 days after insertion in rabbit corneal pockets: A) a representative picture of each implant group, B) angiogenic score means and standard errors measured for eight implant groups.
Figure 9B:
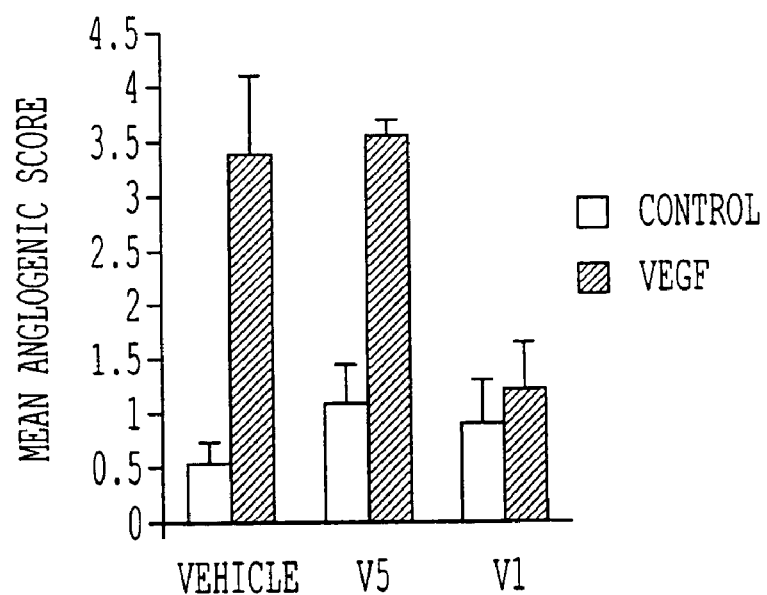
Figure 10A:
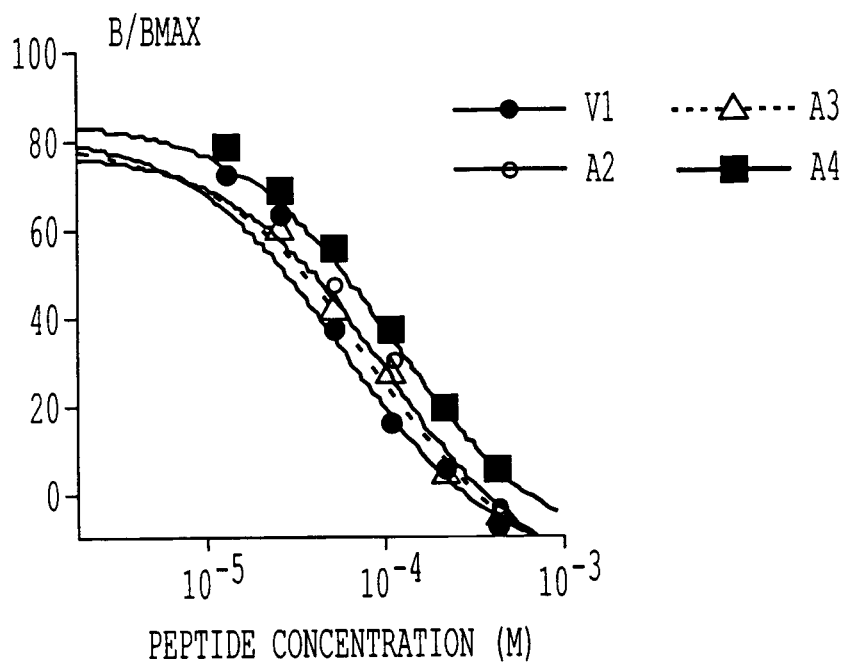
FIG. 10 Displacement curves of 125I-VEGF 165 binding to CHO-KDR transfected cells by the V1 derivatives. The experiment was performed by incubating cells (500,000 cell/well) during 3 hours at +4° C. with 125I-VEGF (Amersham Fr) at a final concentration of 7 pM and increasing concentration of the different peptides analogues (0 to 500 μg/ml) in a final volume of 0.3 ml in the presence of heparin (1 μg/ml). The non specific binding was established in the presence of VEGF 165 (R&D system UK) at a final concentration of 3 nM.
Figure 10B:
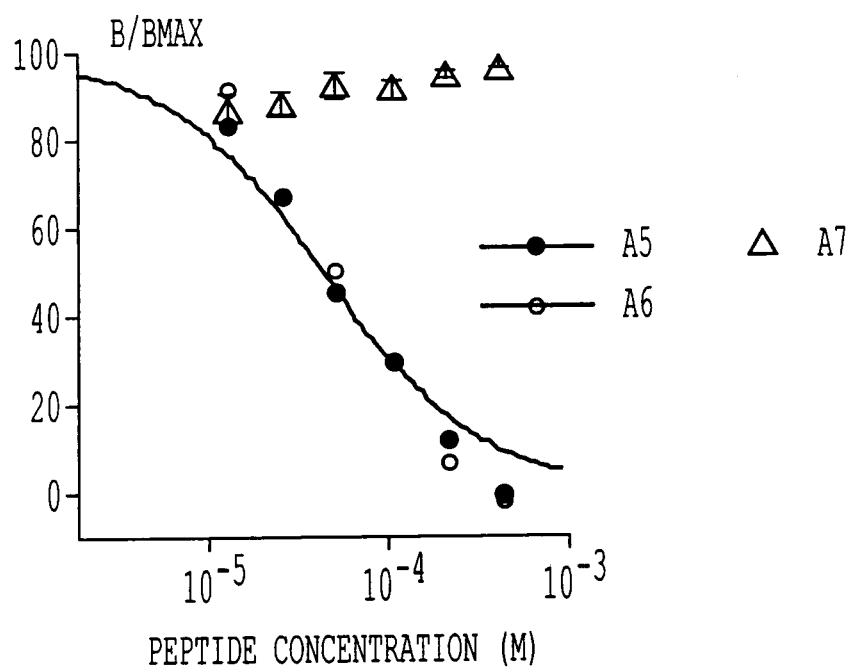

In order to find peptides binding KDR with a higher affinity, we decided to screen the peptide library using an alternative strategy. Peptides mimicking the antigen binding site of many monoclonal antibodies have been isolated successfully from phage-displayed libraries (reviewed in Felici et al., 1995). Screening our repertoire with an anti-VEGF antibody neutralizing its biological activity on endothelial cells would allow us to identify peptides mimicking the KDR binding site on VEGF, and therefore able to block the VEGF-KDR interaction. We first checked if the human anti-VEGF antibody V-4758 could inhibit the proliferation of endothelial cells. Calf Pulmonary Aortic Endothelial cells (CPAE) were used as model cells for VEGF-dependent proliferation. As shown in FIG. 3, the anti-VEGF antibody exerted a dose-dependent inhibitory activity on the proliferation on these cells, and a complete abolition of cell division was achieved in presence of 30 g/ml of antibody. At the same concentration, this antibody had no inhibitory effect on the growth of NIH3T3 fibroblast cells (not shown). These results confirmed that the anti-VEGF antibody could block VEGF-KDR interaction by binding VEGF at the KDR binding site.

Identification of peptides specifically binding the anti-VEGF antibody

The peptide library was then screened by binding to the anti-VEGF antibody. At the end of the selection, 24 clones were isolated and analyzed. DNA sequencing showed that seven independent peptides had been selected (V1 to V7) with no consensus motifs, although a LPP motif was found in two of them (V1 and V6) (Table I).

Figure 2B:
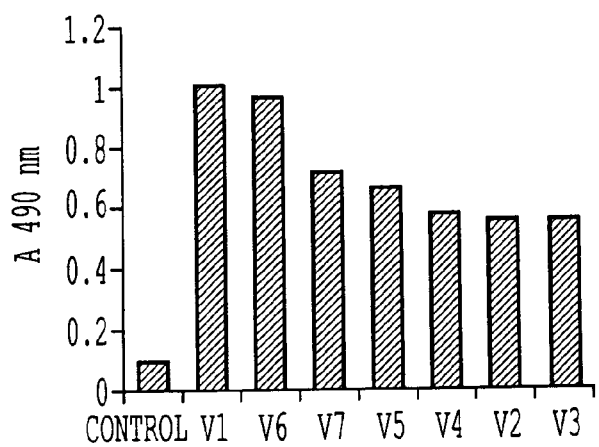

When tested for binding to KDR by ELISA on CHO-KDR cells, all the selected clones gave strong ELISA signals, confirming that they were able to bind the cell receptor (FIG. 2B). Further, they showed higher reactivity than the peptides selected by KDR binding, using phage concentrations ten times lower. This suggests that they had a higher affinity for the receptor. Interestingly, the best reactivities were observed for V1 and V6.

DNA sequence analysis of the selected clones highlights a common LPP/A motif

In order to identify the residues responsible for this increased affinity for KDR, a multiple alignment analysis on all selected sequences was performed. Table II shows that three consensus groups, corresponding to the underlined residues, could be identified. Group A was composed of four clones and was characterized by the motif YX(I/T)(M/P)P (SEQ ID NO:15), the tyrosine residue always occurring in the first position. Two peptides of this group, K1 and V7, shared a strong sequence homology, with three identical residues that are particularly hydrophobic. Group B was characterized by a longer motif HSSLQPRXL (SEQ ID NO:16). Interestingly, two pairs of two clones obtained from different selection strategies show significant homologies, K5 and V4 containing HSSXQ, K7 and V2 with the PRXL motif. A shorter consensus LP(A/P) was found in group C. Interestingly, this group contained the two clones presenting the motif LPP, extended with the K4 clone that has a similar motif LPA. The peptide sequences were also compared to the primary sequence of VEGF (Table II). Alignment of the individual selected clones or of the consensus motifs with VEGF did not produce any significant homology, suggesting that the selected peptides mimicked a discontinuous binding site.

TABLE II

DNA sequence analysis of the selected clones.

Multiple alignment of the selected clones

| (A) | (B) | (C) |
|---|---|---|
| K1 YLTMPTP | K5 HSSLQTP | V1 ATWLPPR |
| V7 YAIMPLV | V4 YHSSFQA | K4 SLPAHAR |
| K6 YSIPKSS | K7 ALQPRYL | V6 LPPNPTK |
| K2 WPTPPYA | V2 NPRALNY | |

Alignment with the VEGF primary sequence

```
         10        20        30        40        50        60
APMAEGGGQNHHEVVKFMDVYQRSYCHPIETLVDIFQEYPDEIEYIFKPSCVPLMRCGGC
         70        80        90       100       110
CNDEGLECVPTEESNITMQIMRIKPHQGQHIGEMSFLQHNKCECRPKKDR (SEQ ID NO:17)
```

Figure 11:
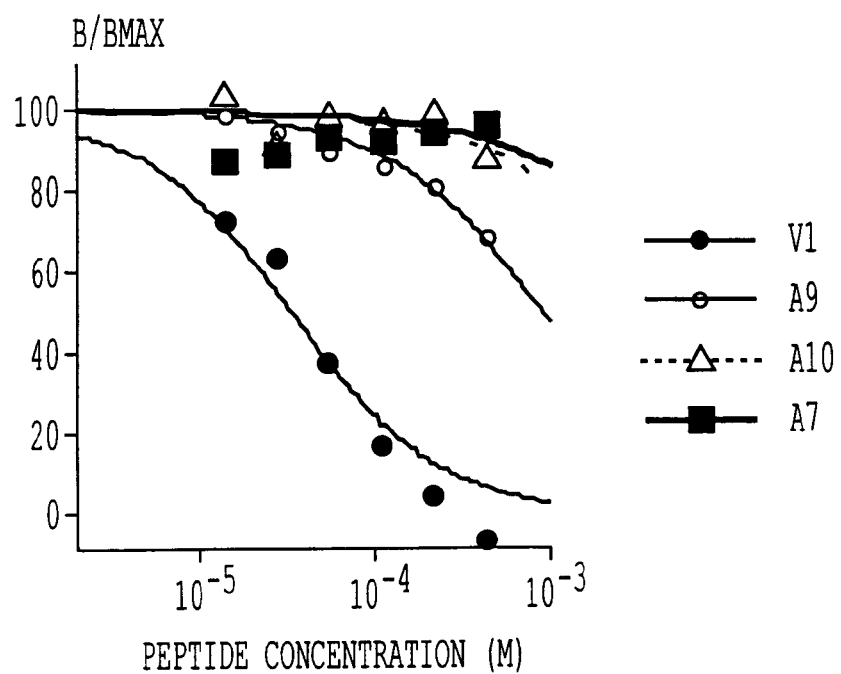
FIG. 11 Comparison of the displacement curves of 125I-VEGF165 binding to CHO-KDR transfected cells by the peptides V1, A9, A10 and A7. Experimental conditions are indicated in the legend of FIG. 10.

V1 Inhibits the Binding of VEGF to KDR

Since the selected peptides were all able to bind KDR, we examined whether they were able to block VEGF interaction with the receptor. Synthetic peptides based on the amino acid sequence of the selected clones were synthesized. They were then tested in competition with VEGF for binding to CHO-KDR cells, using a fixed peptide concentration ($2.1\times10^{-4}$M). Two peptides only, V1 and to a lesser extent K4, showed an inhibitory effect on VEGF binding to KDR at this concentration (FIG. 4). FIG. 5 compares the dose-dependent inhibition of VEGF binding to CHO-KDR cells by VEGF itself (A) or by V1 (B). V1 could nearly block VEGF binding at a 320 M concentration, its $IC_{50}$ being estimated estimated at $8\times10^{-5}$ M. On the contrary, V5 tested in same conditions did not modify VEGF binding. The other peptides binding the anti-VEGF antibody did not show any inhibitory effect of VEGF binding to KDR at this concentration (data not shown).

V1 Specifically Inhibits the Proliferation of Vascular Endothelial Cells

Since the selected peptides could block VEGF binding to KDR, and since endothelial cell proliferation is dependent of VEGF, we tested whether they could inhibit proliferation of endothelial cells in vitro. CPAE cell cultures supplemented with $2.1\times10^{-4}$M synthetic peptides were compared with untreated cultures for cell growth (FIG. 6). After 24 h of incubation, CPAE cell proliferation in presence of V1 was reduced by 60%. Surprisingly, the V6 peptide, which had no effect on VEGF binding to KDR, showed a similar effect. The other peptides also had an inhibitory effect on cell division, but exhibited lower reactivity (about 15%). For all peptides, the inhibitory effects on cell proliferation could be maintained at similar levels in 48 h and 72 h cultures by daily supplementation of the peptides (data not shown).

The ability of V1 to block VEGF-induced proliferation of human endothelial cells was also examined. As shown on FIG. 7A, V1 suppressed the mitogenic activity of VEGF in a dose dependent manner, whereas V5 had no inhibitory effect. To check the specificity of the interaction between V1 and KDR, the same experiment was repeated using KDR anti-idiotypic antibodies (AIA). AIA were generated and found to be selective agonists for KDR, since they promoted endothelial cell proliferation in vitro (data not shown). FIG. 7B shows that unlike V5, V1 could suppress the AIA-dependent cell proliferation, indicating that the VI effect was mediated by a direct interaction with KDR.

To see if this effect was specific of endothelial cells, we tested the effect of V1 on NIH 3T3 fibroblast growth. V1 peptide did not modify the proliferation of these cells, confirming that it blocks VEGF-dependent cell growth only (FIG. 8).

V1 Inhibits Corneal Angiogenesis in vivo

A rabbit corneal pocket assay was used to determine whether V1 could inhibit angiogenesis in vivo. The neovascularization in corneal implants containing VEGF in the presence or absence of peptides was measured (FIGS. 9A and 9B). When compared with the vehicle alone, V1 and V5 did not improve the generation of new blood vessels. VEGF induced a significant angiogenic response, which was not modified by the addition of V5. This stimulatory effect was totally abolished by V1, demonstrating that V1 could inhibit VEGF-induced corneal angiogenesis.

Relationship Between Structure and Activity

A-Analogues from V1 Obtained by Systematic Replacement of an Amino-acid by Alanine (Ala Scan)

Each amino acid of the ATWLPPR (V1) peptide was replaced by a L-alanine residue (AlaScan) as shown in Table III below:

TABLE III

Structure of peptides obtained by systematic replacement of one amino-acid by alanine.

| Peptide | | | | | | | |
|---|---|---|---|---|---|---|---|
| V1 | A | T | W | L | P | P | R |
| A2 | A | A | W | L | P | P | R |
| A3 | A | T | A | L | P | P | R |
| A4 | A | T | W | A | P | P | R |
| A5 | A | T | W | L | A | P | R |
| A6 | A | T | W | L | P | A | R |
| A7 | A | T | W | L | P | P | A |

B-Study of the Efficiency of the V1 Analogues

The effect of the replacement of each amino acid by a L-alanine residue (AlaScan) on binding of I125-VEGF165 to CHO-KDR transfected cells was investigated by measuring the binding of 125I-VEGF in displacement experiments with increasing concentrations of ATWLPPR peptide analogues and analysed by the use of curve fitting, (FIG. 10). The molecule was relatively tolerant to alanine substitution (A2 to A6), except for the Ala7-substituted analogue (A7) which was totally devoid of activity (Table IV).

TABLE IV

Effect (CI50) of the replacement of each amino acid by a L-alanine residue (AlaScan) on binding of VEGF to CHO-KDR transfected cells.

| Analogue | CI50 (×10-5M) | Efficiency (% Emax) |
|---|---|---|
| V1 | 1.88 | 100 |
| A6 | 2.24 | 84 |
| A3 | 2.68 | 70 |
| A5 | 2.91 | 65 |
| A2 | 3.09 | 61 |
| A4 | 6.07 | 31 |
| A7 | | 0 |

C-Specificity of C-terminal Arginine

To determine the specificity of the C-terminal arginine residue its substitution by lysine (A9) and the suppression of this residue (A10), (Table V), have been studied.

TABLE V

Structure of peptides used to study the function of the C-terminal arginine

| Peptide | 1 | 2 | 3 | 4 | 5 | 6 | 7 |
|---|---|---|---|---|---|---|---|
| V1 | A | T | W | L | P | P | R |
| A9 | A | A | W | L | P | P | K |
| A10 | A | T | A | L | P | P | ■ |
| A7 | A | T | W | L | P | P | A |

Displacement curves of 125I-VEGF 165 binding to CHO-KDR transfected cells by the peptide analogues A10 showed that C-terminal region arginine residue deletion significantly reduced the peptide efficiency. The substitution of arginine by lysine (A9) also reduced the peptide efficiency showing that the effect of this arginine residue was not due only to its positive electric charge, (FIG. 11).

Figure 12:
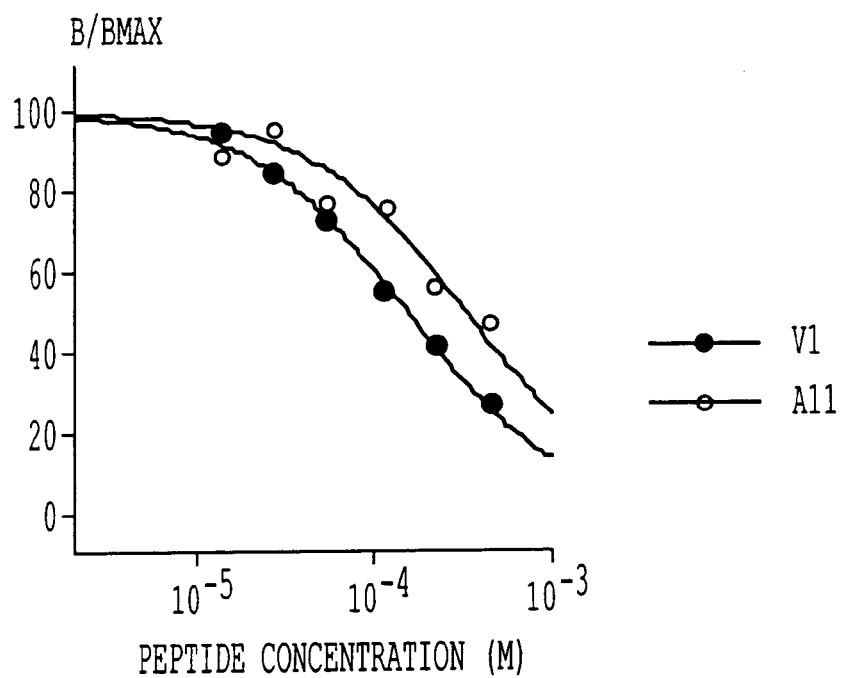
FIG. 12 Displacement curves of 125I-VEGF 165 binding to CHO-KDR transfected cells by the peptides A11 obtained by the substitution of the 6 amino acids upstream to arginine by alanine. Experimental conditions are indicated in the legend of FIG. 10.
Figure 13:
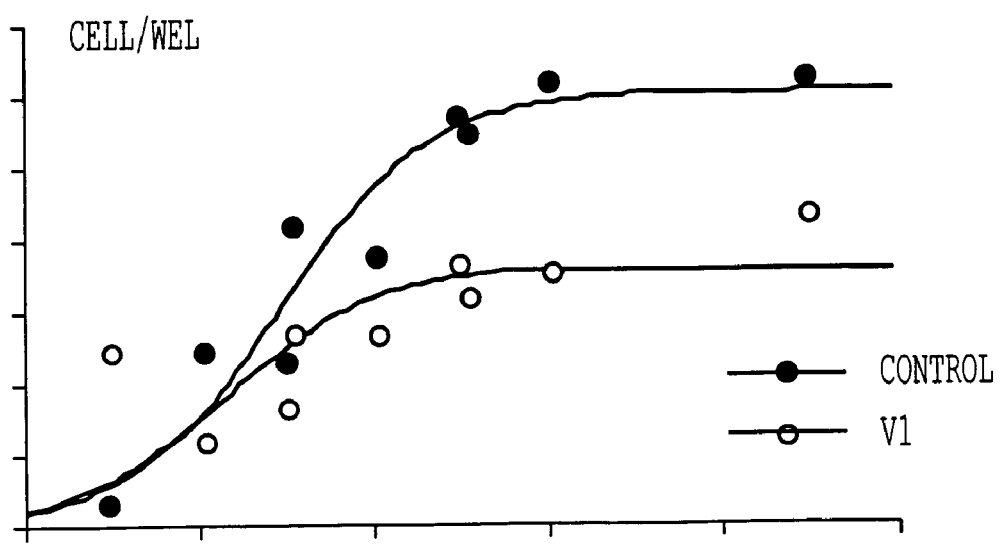
FIG. 13 Effect of V1 (400 μg/ml) VEGF165 induced HUVEC proliferation. Various concentrations of VEGF165 were added during 96 hours.
Figure 14:
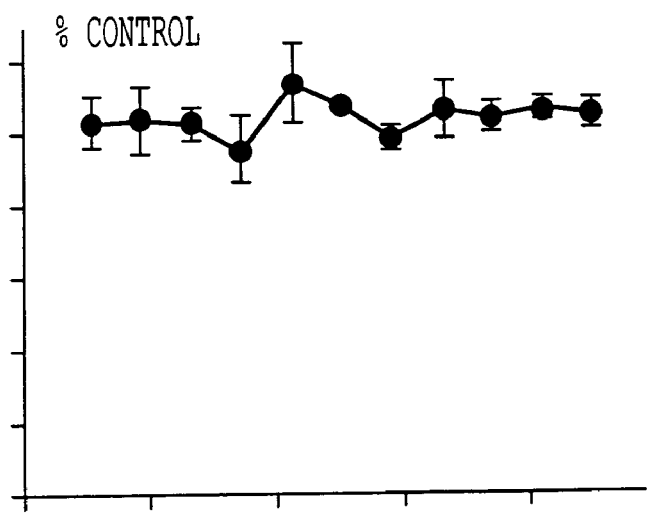
FIG. 14 Effect of V1 on the binding of I125 VEGF 165 to VEGF R2 (KDR)/Fc Chimera (R&D UK). The disulfide linked homodimeric protein were immobilized on the surface of Immulon polystyrene well (Dynatech VA). VEGF was incubated overnight at +4° C. After 3 washings, the bound radio activity was measured.
Figure 15A:
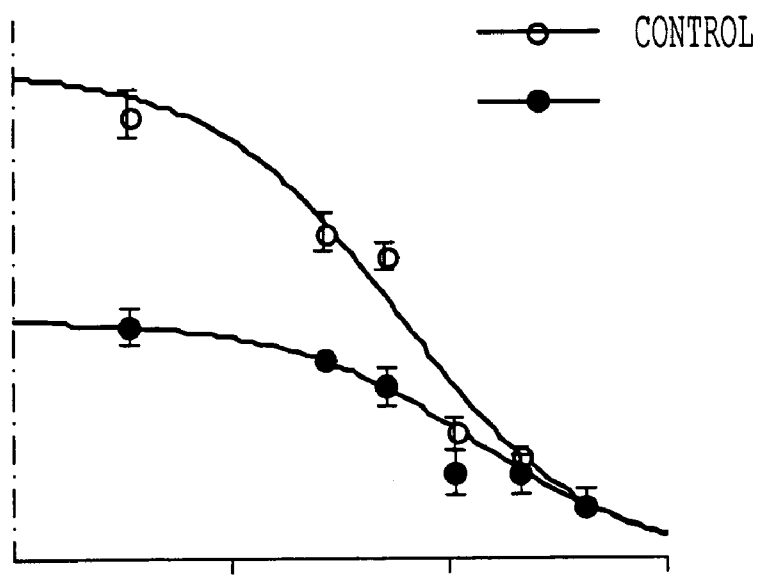
FIGS. 15A and B(A) Displacement curves of 125I-VEGF 165 binding to CHO-KDR transfected cells by VEGF165 at increasing concentrations, in the presence of either saline (open circles) or 50 μg/ml V1 (closed circles). (B) Scatchard representation. Experimental conditions are indicated in the legend of FIG. 10.
Figure 15B:
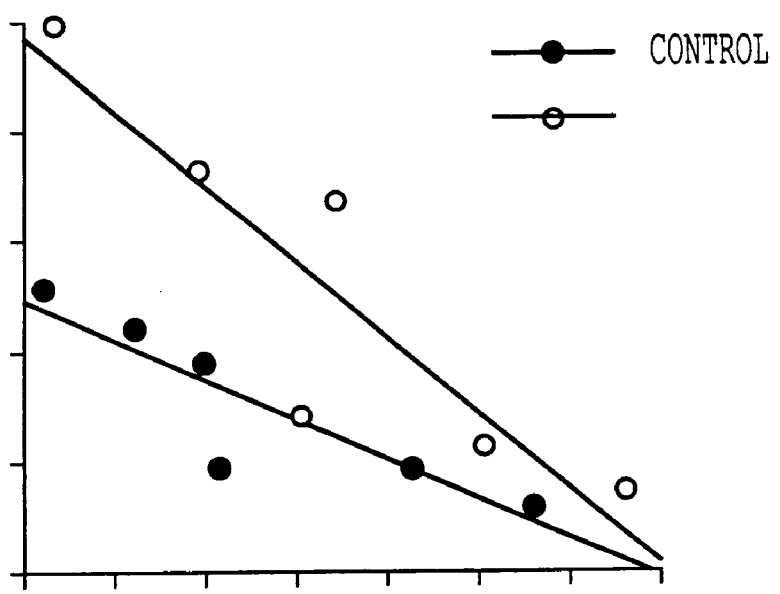
Figure 16A:
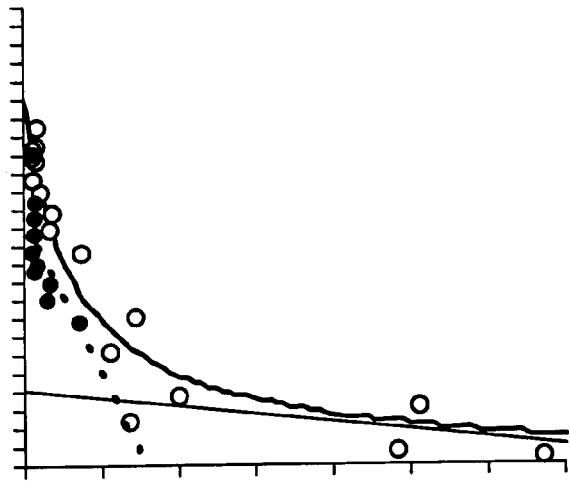
FIGS. 16A and B(A & B) Scatchard representation of 125I-VEGF165 to control HUV-EC cells. (C) Scatchard representation of 125I-VEGF165 to HUV-EC cells in the presence of V140 μg/ml. Experimental conditions are indicated in the legend of FIG. 10.
Figure 16B:
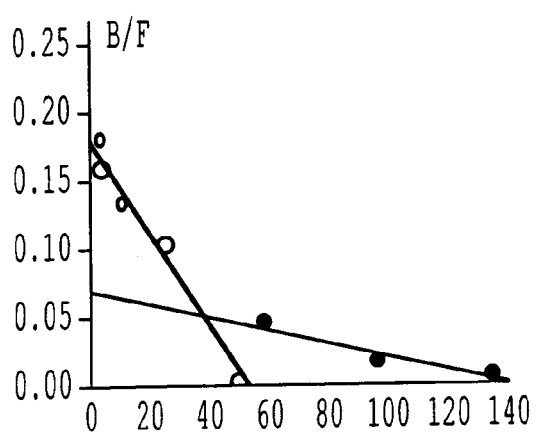
Figure 16C:
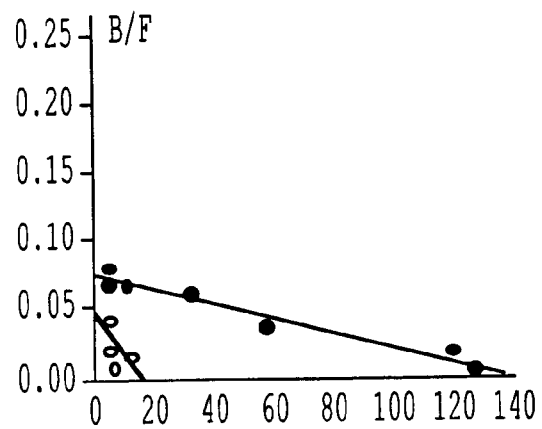
Figure 17:
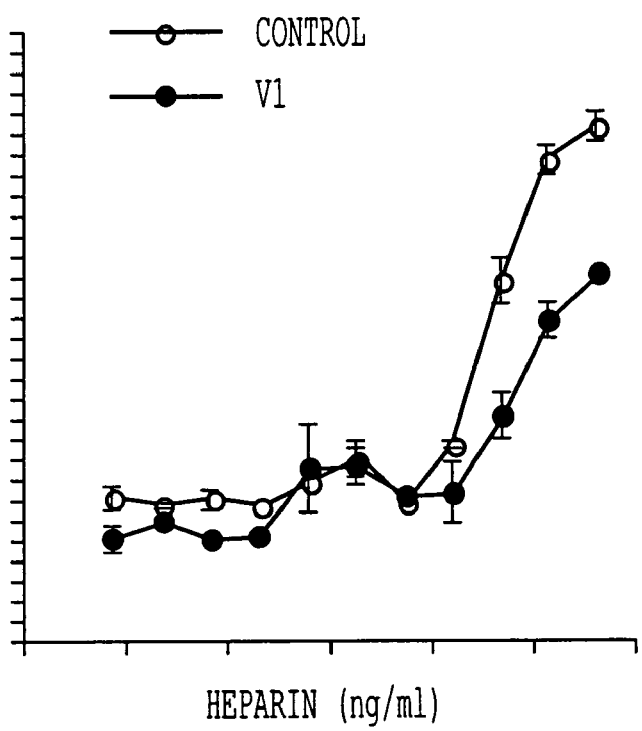
FIG. 17 Heparin effect on binding of I125 VEGF 165 to transfected CHO cell in the presence of either saline (open circles) or V1 peptide (closed circles) at a final concentration of 50 μg/ml. Experimental conditions are indicated in the legend of FIG. 10.
Figure 18:
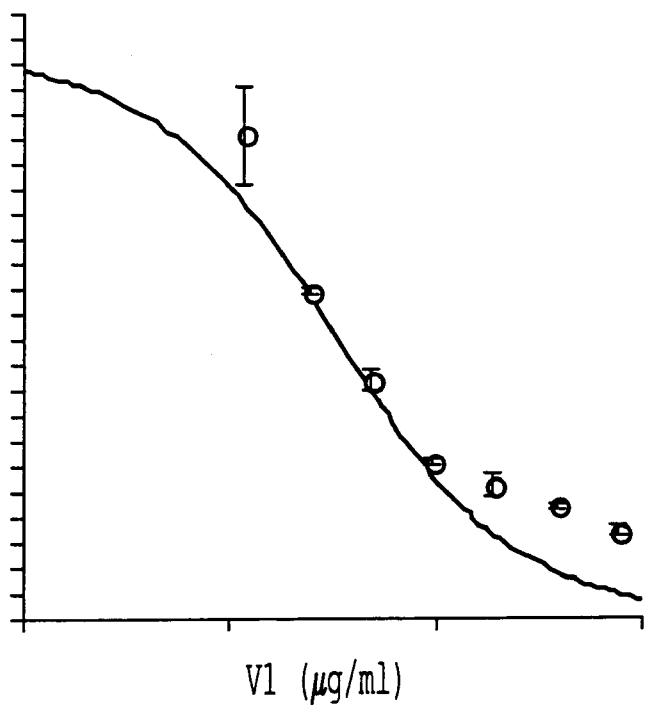
FIG. 18: Displacement curves of 125I-VEGF 165 binding to MDA MB cells by increasing concentrations of V1. Experimental conditions are indicated in the legend of FIG. 10.
Figure 19:
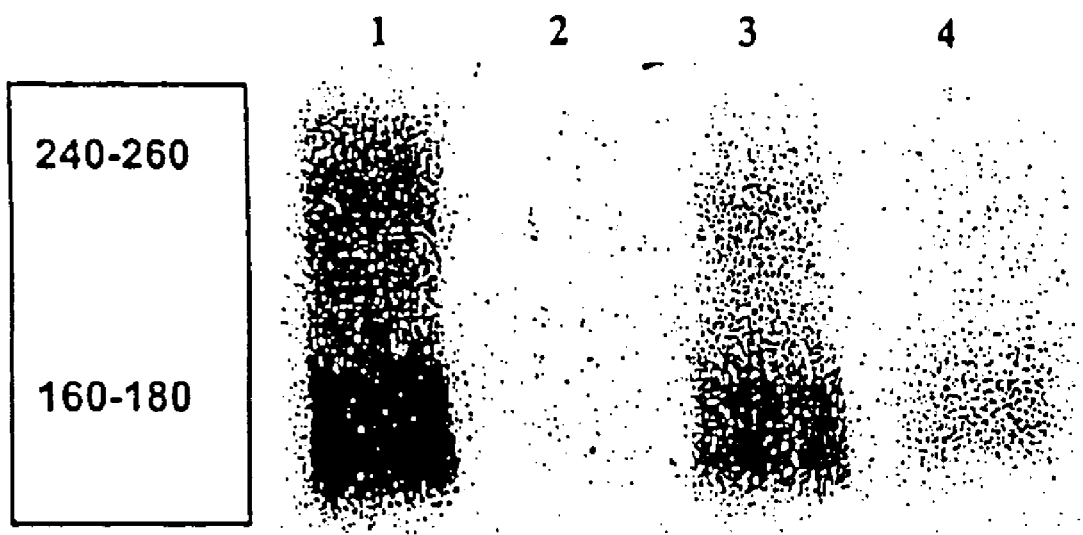
FIG. 19: Cross linking of I125 VEGF165 (160 pM) to HUV-EC cells. 1: Total binding. 2: Non specific binding (VEGF 4.5 nM). 3: V1, ($2.4 \times 10-4M$). 4: V1, ($4.8 \times 10-4M$).

D-Alanine Substitution of the 6 Amino Acids Positioned Upstream the C-terminal Arginine Residue The substitution of the 6 amino acids upstream the C-terminal arginine residue abolished the V1 peptide inhibitory efficiency by a factor 10, (FIG. 12).

The above-results demonstrate that the inhibitory efficiency of V1 is linked to the presence of a C-terminal basic amino-acid (Arg being more potent than Lys) preceded by either aliphatic or aromatic neutral amino acids (including proline).

Action Mechanisms

A-Inhibitory effect of V1 on endothelial cell proliferation

The inhibitory effect of V1 on Human umbilical vein endothelial cell (HUVEC) in primary culture. The VEGF-induced HUVEC proliferation was inhibited by V1 in a non competitive manner (FIG. 13).

B-Effect of V1 on the binding of I125 VEGF165 to recombinant human VEGFR2/Fc chimera V1 was not able to inhibit VEGF binding to VEGF R2 (KDR)/Fc Chimera (FIG. 14).

C Characteristics of the inhibitory effect of V1 on the binding of I125 VEGF 165 to VEGF-R2 expressed by transfected CHO cells:

V1 inhibited the binding of I125 VEGF165 to VR2 expressed by transfected CHO cells. The scatchard binding analysis showed the presence of high affinity specific receptors. This affinity is lowered in the presence of V1 (FIGS. 15 A and B).

D Characteristics of the inhibitory effect of V1 on the binding of I125 VEGF 165 to VEGF-R2 on HUV-EC cells For the analysis of displacement curves of 125I-VEGF 165 binding to HUV-EC, the cells were incubated with VEGF at increasing concentrations, in the presence of either saline or V1 peptide. Scatchard analysis of radioligand receptor binding showed the presence of specific receptors for I125 VEGF165 on the surface of HUV-EC cell line with a Kd of 117 and 2300 pM. V1 inhibited only the VEGF binding to high affinity receptors. (see FIGS. 16A, B and C).

E Interaction of V1 and heparin on the binding of 125I VEGF 165 to VEGF-R2 transfected CHO cells:

The binding of VEGF 165 to transfected CHO cell is agonized heparin-dependent in a concentration range of 10 to 1000 ng/ml. V1 inhibited this heparin agonistic effect. (see FIG. 17)

F Inhibitory effect of V1 on I125 VEGF165 binding to MDA-MB 231 cells:

Breast tumoral cell line MDA-MB 131 has no VEGF-R2 receptors, however they expresses neuropilin 1 (NP1). The binding of 125I VEGF 165 to this cells was inhibited by the V1 peptide. (CI 50=38 $\mu$g/ml) (FIG. 18)

G Effect of the V1 peptide on the cross linking of I125 VEGF165 to HUV-EC.

The cross-linking of I125 VEGF165 to HUV-EC cells showed two labeled 125I-VEGF-receptor complexes. The 240–260 kDa complex could correspond to the VEGF-R2-2EGF165 complex and the 160–170 kDa complex could correspond to the NP1 -VEGF 165 complex. The labeling of the two complexes was decreased in the presence of the V1 peptide. (FIG. 19)

The above-results demonstrate that the mechanism of V1 action involves not only a displacement of VEGF165 from the binding ligand domain of VEGF-R2 but also possible interactions with co-receptors including NP1 and heparan sulfate proteoglycans.

Previous studies have demonstrated that antianogiogenic therapy is a promising approach for the treatment of cancer (Folkman, 1995). Solid tumor growth and tumor metastasis are dependent on tumor vascularization. Moreover, clinical studies of patients with a variety of solid tumors have shown a direct correlation between the density of tumour vessels and a adverse prognosis (Weidner et al., 1991; Albo et al., 1994). VEGF and its signal transducing tyrosine kinase receptor VEGFR-2 (KDR/flk-1) are major mediators of tumor-induced angiogenesis (Terman et al., 1992; Ferrara, 1993). Also, VEGF is different from other growth factors because it acts as an endothelial cell specific mitogen during angiogenesis (Plouët et al., 1989; Leung et al., 1989; Ferrara, 1993). Previous studies have shown that blocking the VEGF—VEGF receptor pathway using antibodies results in murine and human tumor regression (Kim et al., 1993; Cheng et al., 1996). We report here the identification of peptides antagonist for VEGF by use of a phage-displayed peptide library.

There are only limited examples of the direct screening of peptide libraries with a cellular receptor, the main difficulty being the removal of clones binding non-specific determinants. To select peptides binding cell-displayed uPAR (urokinase plasminogen activator receptor), Goodson et al. performed multiple rounds of biopanning using either recombinant Sf9 insect cells or COS-7 cells (1994). In this study, we performed two rounds of negative selection against non recombinant cells at the end of the selection process. This resulted in an efficient removal of non specific clones since all the isolated phage clones could bind KDR specifically on ELISA.

Another possible approach is to screen peptide libraries using antibodies blocking the interaction between receptor and ligand. This assumes that the antibody binding site on the ligand contains residues interacting with the receptor. Using anti-basic fibroblast factor (bFGF) antibodies blocking the binding to its receptor, Yayon et al. (1993) successfully isolated peptides able to inhibit bFGF-induced proliferation of vascular endothelial cells. However, the use of bFGF as a therapeutic target is limited by the fact that it acts on a broad spectrum of cell types and that the in vivo expression of its receptor by endothelial cells is controversial. In contrast, VEGF is a secreted endothelial cell-specific mitogen whose receptors are expressed almost exclusively on vascular endothelial cells and is therefore of greater therapeutic interest (Millauer et al., 1993; Peters et al., 1993). To isolate VEGF antagonists, we used a 7-mer random peptide library displayed on bacteriophage M13 and performed two selections, one based on binding to KDR, and the other on binding to an anti-VEGF blocking antibody. This allowed us to compare the sequences selected by the two strategies, and to identify residues responsible for the antagonist activity.

Library screening for binding to KDR was performed on CHO cells expressing a recombinant receptor at the membrane surface, and we demonstrated that this molecule could bind VEGF similarly to the natural receptor. Indeed, the affinity of the recombinant receptor was comparable to the constant measured on endothelial cells (Terman et al., 1992; Klasgsbrun and D'Amore, 1996). Also, heparin was able to increase VEGF binding to CHO-KDR cells. This phenomenon was bimodal, lower heparin concentration improving the binding of VEGF and higher concentrations having an inhibitory effect, and reproduces the effect of heparin on VEGF binding to natural KDR (Gitay-Goren et al., 1992, 1993). In accordance with previous work, PlGF did not modify VEGF binding to KDR expressing cells (Terman et al., 1994). The reactivity of the peptides selected for KDR binding was relatively low, and only one of them could compete with VEGF for KDR binding at concentrations in the $10^{-4}$ M range. Furthermore, none were potent at suppressing the growth of endothelial cells in vitro, suggesting that the selected peptides bound KDR in regions distant from VEGF binding site and therefore poorly interfered with the VEGF-KDR interaction.

Library screening for antibody binding was an indirect way to isolate peptides antagonist of VEGF-KDR interactions, but nevertheless led to the identification of the most potent peptide. The V1 peptide (ATWLPPR) showed the highest reactivity in ELISA and the highest inhibitory effect on endothelial cell growth. Importantly, V1 inhibited VEGF-induced proliferation of human endothelial cells without influencing the growth of non-endothelial cells and was able to inhibit VEGF-induced angiogenesis in vivo in a rabbit corneal model. This suggests that the effect of V1 was mediated by the direct binding to KDR. Recently, Soker et al. (1998) have identified a new receptor for VEGF which is expressed by endothelial cells and tumor cells. This receptor is identical to human NRP-1, a receptor for the collapsin/semaphorin family that mediates neuronal cell guidance. When co-expressed in cells with KDR, NRP-1 enhanced the binding of VEGF to KDR. Conversely, inhibition of VEGF binding to NRP-1 inhibited its binding to KDR and its subsequent mitogenic activity on endothelial cells. In fact, NRP-1 might be acting as a co-receptor that enhances the VEGF-induced activities mediated by KDR. To see whether V1 reacts specifically with KDR, we tested the binding of V1 to KDR in competition with KDR anti-idiotypic antibodies. We found that V1 was able to block the proliferation of endothelial cells induced by these antibodies, showing that its inhibitory effect was due to a specific interaction with KDR.

Interestingly, V6, which shared the LPP motif in common with V1, significantly inhibited the proliferation of endothelial cells but it did not affect the binding of VEGF to KDR. In contrast, the K4 peptide contained a motif LPA and could partially inhibit VEGF binding to KDR, but had a minor effect on endothelial growth. This suggests that the presence of an alanine residue instead of a proline may account for its lack of reactivity, and that the LPP motif is essential for peptide antagonist activity.

Alignment of the individual selected clones with the primary sequence of the VEGF did not produce any homology. In particular, no LPP motif could be found. This suggests that the KDR binding site on VEGF is discontinuous and that the selected peptides may contain residues distant in the VEGF primary sequence, but in close proximity in the folded molecule. This in accordance with the crystal structure of VEGF which has been recently resolved (Muller et al., 1997). Mutational analysis revealed that two spots of residues involved in KDR binding are located at each pole of the VEGF monomer, that may constitue a functional binding site in the dimer (Muller et al., 1997). We are currently investigating whether residues corresponding to the selected motifs are accessible at the surface of the VEGF dimer and in close proximity in the folded molecule.

Angiogenesis is involved in a variety of human diseases. The VEGF/KDR interaction has been shown to play a role in cancer, but also in diabetic retinopathy (Pierce et al., 1995), psoriasis (Detmar et al., 1994), hemangioblastoma (Wizigmann-Voos et al., 1995), and Kaposi's sarcomas in AIDS patients (Albini et al., 1996). Thus, identification of VEGF antagonists may have potential applications in the treatment of a variety of human diseases. Moreover for therapeutic use, small molecules are preferred since reduced size make them more amenable to translation into organic molecules. Peptides provide leading molecules for the design of unexpensive drugs that can be administered orally.

Our results demonstrate that the ATWLPPR peptide is an effective antagonist of VEGF and an inhibitor of angiogenesis. This peptide could be a potent inhibitor of tumor angiogenesis, and could have a more general interest in diseases in which angiogenesis is involved. In this context, in vivo anti-tumor chemotherapy assays using this peptide must be investigated.

Obviously, numerous modifications and variations on the present invention are possible in light of the above teachings. It is therefore to be understood that within the scope of the appended claims, the invention may be practiced otherwise than as specifically described herein.

REFERENCES

Albini, A., Soldi, R., Giunciuglio, D., Benelli, R., Primo, L., Noonan, D., Salio, M., Camussi, G., Rockl, W. and Bussolino, F. (1996) The angiogenesis induced by HIV-1 tat protein is mediated by the Flk-1/KDR on endothelial cells. *Nat. Med.*, 2, 1371–1375.

Albo, D., Granick, M. S., Jhala, N., Atkinson, B. and Solomon, M. P. (1994) The relationship of angiogenesis biological activity in human squamous cell carcinomas of the head and neck. *Ann. Plastic Surg.*, 32, 588–594.

Ausprunk, D. H. and Folkman, J. (1977) Migration and proliferation of endothelial cells in preformed and newly formed blood vessels during angiogenesis. *Microvasc. Res.*, 14, 53–65.

Boehm, T., Fokman, J., Browder, T. and O'Reilly, M. S. (1997) Antiangiogenic therapy of experimental cancer does not induce acquired drug resistance. *Nature*, 390, 404–407.

Bouck, N., Stellmach, V. and Hsu, S. C. (1996) How tumors become angiogenic. *Adv. in Cancer Res.*, 69, 135–174.

Cheng, S. Y., Huang, H. J. S., Nagane, M., Ji, X. D., Wang, D., Shih, C. C. Y, Arap, W., Huang, C. M. and Cavenee, W. K. (1996) Suppression of glioblastoma angiogenicity and tumorigenicity by inhibition of endogenous expression of vascular endothelial growth factor. *Proc. Natl. Acad. Sci. USA*, 93, 8502–8507.

Cliff, W. J. (1963) Observations on healing tissues: a combined light and electron microscopic investigation. *Philosophical Transactions of the Royal Society*, 246, 305–325.

Cortese, R., Monaci, P., Luzzago, A., Santini, C., Bartoli, F., Cortese, I., Fortugno, P., Galfre, G., Nicosia, A., and Felici, F. (1996) Selection of biologically active peptides by phage display of random peptides libraries. *Curr. Opin. Biotechnol.*, 7, 616–621.

Cwirla, S. E., Peters, E. A., Barrett, R. W. and Dower, W. J. (1990) Peptides of phage: a vast library of peptides for identifying ligands. *Proc. Natl. Acad. Sci., USA*, 87, 6378–6382.

Detmar, M., Brown, L. F., Claffey, K. P., Yeo, K. T., Kocher, O., Jackman, R. W., Berse, B. and Dvorak, H. F. (1994) Overexpression of vascular permeability factor/vascular endothelial growth factor and its receptor in psoriasis. *J Exp. Med.*, 180, 1141–1146.

De Vries, C., Escobedo, J. A., Ueno, H., Houck, K., Ferrara, N. and Williams, L. T. (1992) The fms-like tyrosine kinase, a receptor for vascular endothelial growth factor. *Science*, 255, 989–991.

Esko, J. D. (1991) Genetic analysis of proteoglycan structure, function and metabolism. *Curr. Opin. Cell Biol.*, 3, 805–816.

Favard, C., Moukadiri, H., Dorey, C., Praloran, V. and Plouët, J. (1991) Purification and biological properties of vasculotropin, a new angiogenic cytokine. *Biol. Cell.*, 73, 1–6.

Felici, F., Luzzago, A., Monaci, P., Nicosia, A., Sollazo, M. and Traboni, C. (1995) Peptide and protein display on the surface of filamentous bacteriophage. In Raafat El-Gewely, M. (ed.), *Biotechnology Annual Review.* Amsterdam, The Nederlands: Elsevier, pp.149–183.

Ferrara, N. and Henzel, W. J. (1989) Pituitary follicular cells secrete a novel heparin-binding growth factor specific for vascular endothelial cells. *Biochem. Biophys. Res. Commun.*, 161, 851–858.

Ferrara, N. (1993) Vascular endothelial growth factor. *Trends Cardiovasc. Med.*, 3, 244–250.

Ferrara, N. and Davis-Smyth T. (1997) The biology of vascular endothelial growth factor. *Endocrine Rev.*, 18, 4–25.

Ferrara, N. (1999) Molecular and biological properties of vascular endothelial growth factor. *J Mol. Med.*, 77, 527–543.

Folkman, J. (1995) Angiogenesis in cancer, vascular rheumatoid and other diseases. *Nat. Med.*, 1, 27–30.

Folkman, J.(1995) Clinical applications of research on angiogenesis. *N. Engl. J Med.*, 333, 1757–1763.

Gita-Goren, H., Soker, S., Vlodavsky, I. and Neufeld, G. (1992) The binding of vascular endothelial growth factor to its receptor is dependent on cell surface-associated heparin-like molecules. *J Biol. Chem.*, 267, 6093–6098.

Gita-Goren, H., Halaban, R. and Neufeld, G. (1993) Human melanoma cells but not normal melanocytes express vascular endothelial growth factor receptors. *Biochem. Biophys. Res. Commun.*, 190, 702–709.

Goodson, R. J., Doyle, M. V., Kaufman, S. E. and Rosenberg, S. (1994) High-affinity urokinase receptor antagonists identified with bacteriophage peptide display. *Proc. Natl. Acad. Sci. USA*, 91, 7129–7133.

Hanahan, D. and Folkman, J. (1996) Patterns and emerging mechanisms of the angiogenic switch during tumorigenesis cell. *Cell*, 86, 353–364.

Hoess, R. H. (1993) Phage display of peptide and protein domains. *Curr. Opin. Stuct. Biol.*, 3, 572–579.

Houck K., Ferrara N , Winer J., Cachianes, G., Li, B. and Leung D. W (1991) The vascular endothelial growth factor family: identification of a fourth molecular species and characterization of alternative splicing of RNA. *Molecular Endocrinol.*, 5, 1806–1814.

Houck K., Leung D. W., Rowland A. M., Winer J. and Ferrara N. (1992) Dual regulation of vascular endothelial growth factor biovailability by genetic and proteolytic mechanisms. *J Biol. Chem.*, 267, 26031–26036.

Kerbel R. S. (1991) Inhibition of tumor angiogenesis as a strategy to circumvent acquired resistance to anti-cancer therapeutic agents. *Bioassays*, 13, 31–36.

Kim, K. J., Li, B., Winer, J., Armanini, M., Gillett N., Philips, H. S. and Ferrara, N. (1993) Inhibition of vascular endothelial growth factor-induced angiogenesis suppresses tumor growth in vivo. *Nature*, 362, 841–844.

Klagsbrun, M. and D'Amore, P. A. (1996) Vascular endothelial growth factor and its receptors. *Cytokine Growth Factor Rev.*, 7, 259–270.

Koivunen, E., Gay, D. A. and Ruoslahti, E. (1993) Selection of peptides binding to the 5 1 integrin from phage display library. *J Biol. Chem.*, 268, 20205–20210.

Leung, D. L., Cachianes, G., Kuang, W.6.J., Goeddel, D. V. anf Ferrara, N. (1989) Vascular endothelial growth factor is a secreted angiogenic mitogen. *Science*, 246, 1306–1309.

Matthews, W., Jordan, C. T., Gavin, M., Jenkins, N. A., Copeland, N. G. and Lemischka, I. R. (1991) A receptor tyrosine kinase, cDNA isolated from a population of enriched primitive hematopoietic cells and exhibiting close genetic linkase to c-kit. *Proc. Natl. Acad. Sci. USA*, 88, 9026–9030.

Millauer, B., Wizigmann-Voos, S., Schnürch, H., Martinez, R., Moller, N. P. H., Risau, W. and Ullrich, A. (1993) High affinity VEGF binding and developmental expression suggest Flk-1 as a major regulator of vasculogenesis and angiogenesis. *Cell*, 72, 835–846.

Muller, Y. A., Christinger, H. W., Bruce, A. K. and De Vos, A. M. (1997) The crystal structure of vascular endothelial growth factor (VEGF) refined to 1.93 A resolution: multiple copy flexibility and receptor binding. *Stucture*, 5, 1325–1338.

Muller, Y. A., Li, B., Christinger, H. W., Wells, J. A., Cunningham, B. C. and De Vos, A. M. (1996) Vascular endothelial growth factor: crystal structure and functional mapping of the kinase domain receptor binding site. *Proc. Natl. Acad. Sci. USA*, 94, 7192–7197.

Myoken, Y., Kayada, Y., Okamoto, T., Kan, M., Sato, G. H. and Sato, J. D. (1991) Vascular endothelial cell growth factor (VEGF) produced by A-431 human eperdimoid carcinoma cells and identification of VEGF membrane binding sites. *Proc. Natl. Acad. Sci. USA*, 88, 5819–5823.

O'Neil, K. T., Hoess, R. H., Jackson, S. A., Ramachandran, N. S., Mousa, S. A. and Degrado W. F. (1992) Identification of novel peptide antagonists for gpIIB/IIIa from a conformationnnaly constrained phage peptide library. *Proteins*, 14, 509–515.

Ortéga N., Jonca F., Vincent S., Favard C., Malavaud B., Ruchoux M—M, Plouët J. (1997) Systemic activation of the vascular endothelial growth factor receptor flk-1 selectively triggers angiogenic endothelial cells. *Am. J Pathol.*, 151, 1215–1224.

Peters, K. G., De Vries, C. and Williams, L. T. (1993) Vascular endothelial growth factor receptor expression during embryogenesis and tissue repair suggests a role in endothelial differentiation and blood vessel growth. *Proc. Nati. Acad. Sci. USA*, 90, 8915–8919.

Pierce, E. A., Avery, R. L., Foley, E. D., Aiello, L. P. and Smith, L. R. H. (1995) Vascular endothelial growth factor/ vascular permeability factor expression in a mouse model of retinal neovascularization. *Proc. Natl. Acad. Sci. USA*, 92, 905–909.

Plouët, J., Schilling, J. and Gospodarowicz, D. (1989) Isolation and characterization of newly identified endothelial cell mitogen produced by AtT-20 cells. *EMBO J.*, 8, 3801–3806.

Plouët, J., Moro, F., Bertagnolli, S., Coldeboeuf, N., Mazarguil, H., Clamens, S. and Bayard, F. (1997) Extracellular cleavage of the vascular endothelial growth factor 189 -amino acid form by urokinase is required for its mitogenic effect. *J Biol. Chem.*, 272, 13390–13396.

Scatchard, G. (1986) The attraction of proteins for small molecules and ions. *Ann. NY Acad. Sci.*, 261, 4660–4662.

Schoefl, G. I. (1963) Studies on inflammation. III. Growing capillaries: their structure and permeability. *Virchows Arch. Pathol. Anat.*, 337, 97–141.

Smith, G. P. (1985) Filamentous fusion phage: novel expression vectors that display cloned antigens on the virion surface. *Science*, 228, 1315–1317.

Soker, S., Takashima, S., Miao, H. Q., Neufeld, G. and Klagsbrun, M. (1998) Neuropilin-1 is expressed by endothelial and tumor cells as an isoform-specific receptor for vascular endothelial growth factor. *Cell*, 92, 735–745.

Tennan, B. I., Carrion, M. E., Kovacs, E., Rasmussen, B. A., Eddy, R. L. and Shows, T. B. (1991) Identification of a new endothelial growth factor receptor tyrosine kinase. *Oncogene*, 6, 1677–1683.

Terman, B., Dougher-Vermazen, M., Carrion, M., Dimitrov, D., Armellino, D., Gospodarowicz, D., and Bohlen, P. (1992) Identification on the KDR tyrosine kinase as a receptor for vascular endothelial growth factor *Biochem. Biophys. Res. Commun.*, 187, 1579–1586.

Terman, B. I., Khandke, L., Dougher-Vermazan, M., Maglione, D., Lassam, N. J., Gospodarowicz, D., Persico, M. G., Bohlen, P. and Eisenger M. (1994) VEGF receptor subtypes KDR and FLT1 show different sensitivities to heparin and placenta growth factor. *Growth factor*, 11, 187–195.

Tisher, E., Mitchell, R., Hartman, T., Silva, M., Gospodarowicz, D., Fiddes, J. C. and Abraham, J. A. (1991) The human gene for vascular endothelial growth factor. Multiple protein forms are encoded through alternative exon splicing. *J Biol. Chem.*, 266, 11947–11954.

Thorpe, P. E and Burrows, F. J. (1995) Antibody-directed targeting of the vasculature of solid tumors. *Breast Cancer Research and Treatments*, 36, 237–251.

Waltenberger, J., Claesson-Welsh, L., Siegbahn, M. and Heldin, C. H. (1994) Different signal transduction properties of KDR and FLT-1, two receptors for vascular endothelial growth factor. *J Biol. Chem.*, 269, 26988–26995.

Watters, J. M., Telleman, P. and Junghans R. P. (1997) An optimized method for cell-based phage displayed panning. Immunotechnol., 3, 21–29.

Weidner, N., Semple, J. P., Welch, W. R. and Folkman, J. (1991) Tumor angiogenesis and metastasis-correlation in invasive breast carcinoma. *N. Engl. J Med.*, 324, 1–8.

Wizigmann-Voos, S., Breier, G., Risau, W. and Plate, K. H. (1995) Up-regulation of vascular endothelial growth factor and its receptor in von Hippel-Lindau disease-associated and sporadic hemangioblastomas. *Cancer Res.*, 55, 1358–1364.

Yayon, A., Aviezer, D., Safran, M., Gross, J. L., Heldman, Y., Cabilly, S., Givol, D. and Katchalski-Katzir, E. (1 993) Isolation of peptides that inhibit binding of basic fibroblast growth factor to its receptor from a random phage-epitope library. *Proc. Natl. Acad. Sci. USA*, 90, 10643–10647.

Young, R. C. (1989) Drug resistance: the clinical problem. *Cancer treat. Res.*, 48, 1–12.

What is claimed is:

1. A purified peptide selected from the group consisting of SEQ ID NO:8, SEQ ID NO:9, SEQ ID NO:10, SEQ ID NO:11, SEQ ID NO:12, SEQ ID NO:13, SEQ ID NO:14; wherein said peptide inhibits the binding of VEGF to KDR.

2. The peptide of claim 1, wherein said peptide is SEQ ID NO:11.

3. A purified peptide selected from the group consisting of SEQ ID NO:1, SEQ ID NO:2, SEQ ID NO:3, SEQ ID NO:4, SEQ ID NO:5, SEQ ID NO:6, SEQ ID NO:7; wherein said peptide inhibits the binding of anti-VEGF antibody to VEGF.

4. The peptide of claim 3, wherein said peptide is SEQ ID NO:1.

5. A purified peptide of the sequence ATWLPPR (SEQ ID NO:1).

6. The peptide of claim 5, wherein said peptide is capable of interacting with VEGF.

7. The peptide of claim 5, wherein said peptide is capable of inhibiting the interaction between VEGF and KDR.

8. The peptide of claim 5, wherein said peptide is capable of inhibiting the proliferation of vascular endothelial cells mediated by VEGF.

9. The peptide of claim 5, wherein said peptide is capable of inhibiting angiogensis mediated by VEGF.

10. A pharmaceutical composition comprising the peptide of claim 1 and a pharmaceutically acceptable carrier.

11. A pharmaceutical composition comprising the peptide of claim 3 and a pharmaceutically acceptable carrier.

12. A pharmaceutical composition comprising the peptide of claim 5 and a pharmaceutically acceptable carrier.

13. A method of inhibiting angiogenesis in a patient comprising administering to said patient an effective amount of the peptide of claim 5 to inhibit angiogenesis.

* * * * *

```
SEQUENCE LISTING

<160> NUMBER OF SEQ ID NOS: 17

<210> SEQ ID NO 1
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Ala Thr Trp Leu Pro Pro Arg
1               5

<210> SEQ ID NO 2
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Asn Pro Arg Ala Leu Asn Tyr
1               5

<210> SEQ ID NO 3
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 3

Ala Asn Leu Phe Lys Ala Lys
1               5

<210> SEQ ID NO 4
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE
```

```
<400> SEQUENCE: 4

Tyr His Ser Ser Phe Gln Ala
1               5

<210> SEQ ID NO 5
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 5

Ile Leu Asp Asn Tyr Lys Leu
1               5

<210> SEQ ID NO 6
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 6

Leu Pro Pro Asn Pro Thr Lys
1               5

<210> SEQ ID NO 7
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

Tyr Ala Ile Met Pro Leu Val
1               5

<210> SEQ ID NO 8
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 8

Tyr Leu Thr Met Pro Thr Pro
1               5

<210> SEQ ID NO 9
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9

Trp Pro Thr Pro Pro Tyr Ala
1               5

<210> SEQ ID NO 10
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE
```

```
<400> SEQUENCE: 10

Thr Pro His Asn Thr Val Ser
1               5

<210> SEQ ID NO 11
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 11

Ser Leu Pro Ala His Ala Arg
1               5

<210> SEQ ID NO 12
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 12

His Ser Ser Leu Gln Thr Pro
1               5

<210> SEQ ID NO 13
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 13

Tyr Ser Ile Pro Lys Ser Ser
1               5

<210> SEQ ID NO 14
<211> LENGTH: 7
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 14

Ala Leu Gln Pro Arg Tyr Leu
1               5

<210> SEQ ID NO 15
<211> LENGTH: 5
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (2)..(2)
<223> OTHER INFORMATION: X = ANY AMINO ACID
<221> NAME/KEY: MISC_FEATURE
<222> LOCATION: (3)..(3)
<223> OTHER INFORMATION: X = I OR T
<221> NAME/KEY: MISC_FEATURE
<222> LOCATION: (4)..(4)
<223> OTHER INFORMATION: X = M OR P

<400> SEQUENCE: 15

Tyr Xaa Xaa Xaa Pro
1               5
```

```
<210> SEQ ID NO 16
<211> LENGTH: 9
<212> TYPE: PRT
<213> ORGANISM: ARTIFICIAL SEQUENCE
<220> FEATURE:
<223> OTHER INFORMATION: SYNTHETIC PEPTIDE
<221> NAME/KEY: MISC_FEATURE
<222> LOCATION: (8)..(8)
<223> OTHER INFORMATION: X = ANY AMINO ACID

<400> SEQUENCE: 16

His Ser Ser Leu Gln Pro Arg Xaa Leu
1               5

<210> SEQ ID NO 17
<211> LENGTH: 110
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 17

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg
                100                 105                 110
```